(12) United States Patent
Griffin

(10) Patent No.: US 12,367,895 B2
(45) Date of Patent: Jul. 22, 2025

(54) GROUP MULTIDIMENSIONAL MENTAL STATE PREDICTION

(71) Applicant: Insight Direct USA, Inc., Tempe, AZ (US)

(72) Inventor: Michael Griffin, Wayland, MA (US)

(73) Assignee: Insight Direct USA, Inc., Chandler, AZ (US)

( * ) Notice: Subject to any disclaimer, the term of this patent is extended or adjusted under 35 U.S.C. 154(b) by 382 days.

(21) Appl. No.: 17/951,960

(22) Filed: Sep. 23, 2022

(65) Prior Publication Data

US 2023/0172563 A1 Jun. 8, 2023

Related U.S. Application Data

(60) Provisional application No. 63/405,725, filed on Sep. 12, 2022, provisional application No. 63/405,726, (Continued)

(51) Int. Cl.

| | |
|---|---|
| G10L 25/63 | (2013.01) |
| A61B 5/00 | (2006.01) |
| A61B 5/16 | (2006.01) |
| G06F 40/30 | (2020.01) |
| G06V 10/22 | (2022.01) |
| G06V 10/44 | (2022.01) |
| G06V 10/70 | (2022.01) |
| G06V 20/40 | (2022.01) |

(Continued)

(52) U.S. Cl.
CPC .............. *G10L 25/63* (2013.01); *A61B 5/165* (2013.01); *A61B 5/4803* (2013.01); *A61B 5/7275* (2013.01); *G06F 40/30* (2020.01); *G06V 10/22* (2022.01); *G06V 10/44* (2022.01); *G06V 10/70* (2022.01); *G06V 20/41* (2022.01); *G06V 20/46* (2022.01); *G06V 40/171* (2022.01); *G06V 40/20* (2022.01)

(58) Field of Classification Search
CPC ....... G10L 25/63; G06F 40/30; G06V 40/171; G06V 20/46; G06V 10/70; G06V 20/41; G06V 10/44; G06V 10/22; G06V 40/20; A61B 5/165; A61B 5/4803; A61B 5/7275
USPC ........................................................ 600/301
See application file for complete search history.

(56) References Cited

U.S. PATENT DOCUMENTS

| 2014/0093849 A1 | 4/2014 | Ahn et al. |
|---|---|---|
| 2016/0358085 A1 | 12/2016 | Abadi et al. |

(Continued)

*Primary Examiner* — Aaron F Roane
(74) *Attorney, Agent, or Firm* — Kinney & Lange, P.A.

(57) ABSTRACT

A method of predicting an group mental state according to the present disclosure includes acquiring video data of a first individual and a second individual, extracting first image data of the first individual from the video data, extracting first audio data of the first individual from the video data, extracting second image data of the first individual from the video data, extracting second audio data of the first individual from the video data, extracting first semantic text data from the first audio data, and extracting second semantic text data from the second audio data. The method further includes identifying a first set of features, identifying a second set of features, predicting a first mental state value, predicting a second mental state value, predicting a third mental state value, predicting a fourth mental state value, and generating first and second average mental state values.

20 Claims, 8 Drawing Sheets

Related U.S. Application Data filed on Sep. 12, 2022, provisional application No. 63/286,844, filed on Dec. 7, 2021.

(51) Int. Cl.
  *G06V 40/16* (2022.01)
  *G06V 40/20* (2022.01)

(56) References Cited

U.S. PATENT DOCUMENTS

| | | |
|---|---|---|
| 2019/0012599 A1 | 1/2019 | El Kaliouby et al. |
| 2020/0138356 A1 | 5/2020 | Sharon et al. |
| 2021/0000404 A1 | 1/2021 | Wang et al. |
| 2021/0191506 A1 | 6/2021 | Wang et al. |
| 2021/0287697 A1 | 9/2021 | Marti et al. |
| 2021/0339759 A1* | 11/2021 | Fouad .................. B60W 50/14 |
| 2021/0352380 A1 | 11/2021 | Duncan et al. |
| 2022/0270636 A1 | 8/2022 | Tao et al. |

* cited by examiner

GROUP MULTIDIMENSIONAL MENTAL STATE PREDICTION

CROSS-REFERENCE TO RELATED APPLICATION(S)

This application claims the benefit of U.S. Provisional Application No. 63/286,844 filed Dec. 7, 2021 for "MACHINE LEARNING METHOD TO QUANTIFY PRESENT STATE-OF-MIND AND PREDICT FUTURE STATE-OF-MIND OF ONE OR MORE INDIVIDUALS BASED ON VIDEO IMAGES OF THOSE INDIVIDUALS" by M. Griffin, H. Kotvis, K. Lumb, K. Poulson, and J. Miner, the disclosure of which is incorporated in its entirety by reference herein; of U.S. Provisional Application No. 63/405,726 filed Sep. 12, 2022 for "MULTIDIMENSIONAL MENTAL STATE PREDICTION" by M. Griffin, the disclosure of which is incorporated in its entirety by reference herein; and of U.S. Provisional Application No. 63/405,725 filed Sep. 12, 2022 for "GROUP MULTIDIMENSIONAL MENTAL STATE PREDICTION" by M. Griffin, the disclosure of which is also incorporated in its entirety by reference herein.

BACKGROUND

The present disclosure relates to mental state prediction and, more particularly, systems and methods for predicting mental state using video data.

Individuals convey information through multiple ways, including verbal and non-verbal means. In conversational or social interactions, interpreting verbal and non-verbal information simultaneously and in real-time can be difficult. Further, some individuals have impairments or disabilities that can significantly increase the difficulty of interpreting verbal and/or non-verbal information.

SUMMARY

An embodiment of a method of predicting a group mental state according to the present disclosure includes acquiring video data of a first individual and a second individual, extracting first image data of the first individual from the video data, extracting first audio data of the first individual from the video data, extracting second image data of the first individual from the video data, extracting second audio data of the first individual from the video data, extracting first semantic text data from the first audio data, and extracting second semantic text data from the second audio data. The method further includes identifying a first set of features, identifying a second set of features, predicting a first mental state value, predicting a second mental state value, predicting a third mental state value, predicting a fourth mental state value, and generating first and second average mental state values. The first set of features is identified based on at least one of the first image data, the first audio data, and the first semantic text data. The second set of features is identified based on at least one of the second image data, the second audio data, and the second semantic text data. The first and second sets of features are identified by a first computer-implemented machine learning mode. The first and second mental state values describe a first mental state and are predicted by a second computer-implemented machine learning model. The third and fourth mental state values describe a second mental state and are predicted by a third computer-implemented machine learning model. The first and third mental state values are predicted based on the first set of features and the second and fourth mental state values are predicted based on the second set of features. The first average mental state value is generated by averaging the first mental state value and the second mental state value. The second average mental state value is generated by averaging the third mental state value and the fourth mental state value.

An embodiment of a system for predicting a group mental state according to the present disclosure includes processor, a user interface, and memory. The user interface is configured to enable an operator to interact with the processor. The memory is encoded with instructions that, when executed, cause the processor to acquire video data of a first individual and a second individual, extract first image data of the first individual from the video data, extract first audio data of the first individual from the video data, extract second image data of the second individual from the video data, extract second audio data of the second individual from the video data, extract first semantic text data from the first audio data, and extract second semantic text data from the second audio data. The instructions further cause the processor to identify a first set of features from at least one of the first image data, the first audio data, and the first semantic text data, and also to identify a second set of features from at least one of the second image data, the second audio data, and the second semantic text data. The first and second sets of features are identified by a first computer-implemented machine learning model. The instructions further cause the processor to predict first, second, third, and fourth mental state values with a second computer-implemented machine learning model. The first mental state value is based on the first set of features and describes a first mental state, the second mental state value is based on the second set of features and describes the first mental state, the third mental state value based on the first set of features and describes a second mental state, and the fourth mental state value is based on the second set of features and describes. the second mental state. The instructions also cause the processor to generate first and second average mental state values. The first average mental state value is generated by averaging the first mental state value and the second mental state value, and the second average mental state value is generated by averaging the third mental state value and the fourth mental state value.

A further embodiment of a method of predicting a group mental state according to the present disclosure includes acquiring video data, extracting first image data of a first individual from the video data, extracting first audio data of the first individual from the video data, extracting second image data of a second individual from the video data, extracting second audio data of the second individual from the video data, extracting third image data of a third individual from the video data, extracting third audio data of the third individual from the video data, extracting first semantic text data from the first audio data, extracting second semantic text data from the second audio data, and extracting third semantic text data from the third audio data. The method further includes identifying a first set of features, identifying a second set of features, identifying a third set of features, and predicting first, second, third, fourth, fifth, and sixth mental state values. The method further includes generating first and second average mental state values, recalling a multidimensional mental state model, and generating an overall group mental state for a group comprising the first individual, the second individual, and the third individual. The video data portrays the first individual, the second individual, and the third individual. The first set of features is identified based on at least one of the first image data, the first audio data, and the first semantic text data. The second set of features is identified based on at least one of the second image data, the second audio data, and the second semantic text data. The third set of features is identified based on at least one of the third image data, the third audio data, and the third semantic text data. The first, second, and third sets of features are identified by a first computer-implemented machine learning mode. The first, second, and fifth mental state values describe a first mental state and are predicted by a second computer-implemented machine learning model. The third, fourth, and sixth mental state values describe a second mental state and are predicted by a third computer-implemented machine learning model. The first and third mental state values are predicted based on the first set of features, the second and fourth mental state values are predicted based on the second set of features, and the fifth and sixth mental state values are predicted based on the third set of features. The first average mental state value is generated by averaging the first mental state value, the second mental state value, and the fifth mental state values. The second average mental state value is generated by averaging the third mental state value, the fourth mental state value, and the sixth mental state value. The multidimensional mental state model is recalled from a memory. A first dimension of the multidimensional mental state model describes the first mental state and a second dimension of the multidimensional mental state model describes the second mental state. The overall group mental state is generated based on the multidimensional mental state model, the first average mental state value, and the second average mental state value.

DETAILED DESCRIPTION

Figure 1:
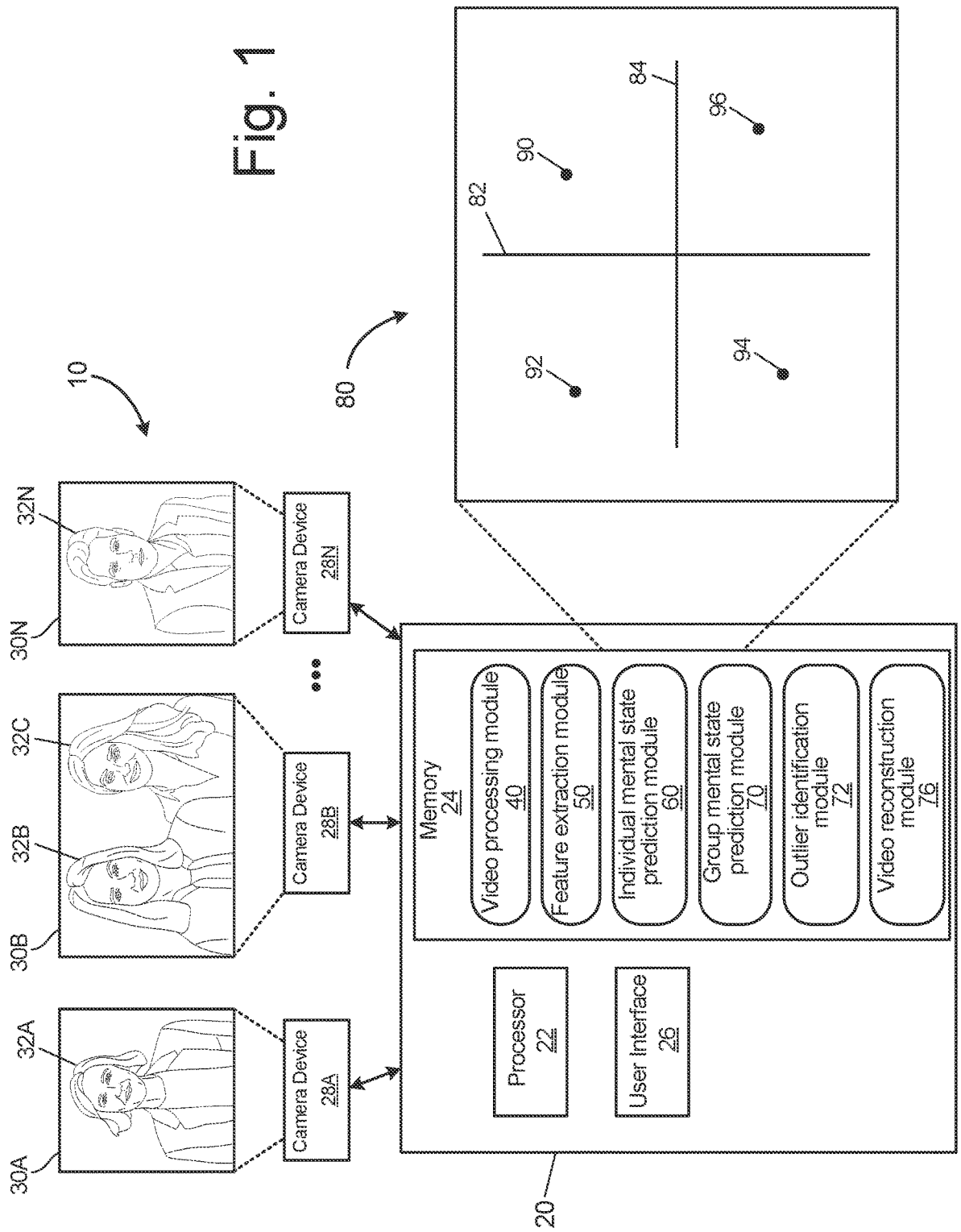
FIG. 1 is a schematic diagram of an example of a mental state classifier.

The present disclosure relates to systems and methods for predicting state of mind of a group of individuals captured in video data. More specifically, the present disclosure relates to systems and methods for predicting state of mind for each individual in a group and for predicting an overall state of mind for the group based on the individual state of mind predictions. As will be explained in more detail subsequently, the systems and methods disclosed herein allow for prediction of group mental state using a multidimensional mental state model that assign different aspects of mental state to different dimensions of the model, thereby significantly improving the resolution and accuracy of mental state predictions as compared to existing models of mental state.

As used herein, "mental state" refers to the attitude, mood, and/or emotion of an individual. The mental state of an individual can be significantly more complex than, for example, an emotion of the individual. Existing methods can use video data to identify discrete emotions and are not capable of identifying more complex mental states. As will be explained in substantially more detail subsequently, the multidimensional mental state models described herein advantageously are able to distinguish and identify an individual's mental state, as opposed to simply identifying the individual's emotion. For example, existing methods focused on emotion may be limited to simple emotional states such as "happy," "sad," "neutral," or "afraid," while a multidimensional mental state model according to the present disclosure can be used to identify more complex mental states, such as "bored," "satisfied," "sleepy," or "content" in addition to the emotional states identifiable by simpler existing methods.

Further, the multidimensional mental state models described herein allow for mental state to be determined based on the extent to which an individual is experiencing various mental state components that contribute to an overall mental state. For example, it is possible for an individual to be simultaneously or substantially simultaneously experiencing two or more emotions, attitudes, and/or moods in varying degrees. Each emotion, attitude, and/or mood can be described by a dimension of the multidimensional mental state model, allowing the individual's overall mental state to be determined with significantly more accuracy and granularity than existing methods that use a single emotion, attitude, and/or mood to describe mental state.

As will be explained in more detail subsequently, the systems and methods disclosed herein enable the prediction of an overall mental state for a group of individuals. As will be explained in detail subsequently, a group member or individual interacting with a group can use a single group mental state generated using the systems and methods disclosed herein to obtain a general understanding of group mental state without having to separately evaluate mental states of each individual in the group.

Current methods of estimating individual attitude or emotion specialize in extremely narrow use cases (e.g., analyzing the alertness of automobile drivers or eye-tracking to gauge a person's attention level). These existing methods extract only a small fraction of the emotion information contained in the video feed and do not attempt to analyze more than one individual at a time. Advantageously, the systems disclosed herein are capable of analyzing multiple individuals in a group, of determining a single value reflective of an overall group mental state. Notably, as the methods herein are configured to use multidimensional mental state model rather than a simpler, existing emotion model, the systems and methods disclosed herein can be applied to a wide variety of applications and use cases, reducing the need for the development of use-case specific models to understand mental state.

The present disclosure also provides systems and methods for predicting mental state using data contained in a video file or video stream. Image, audio, and text data can be extracted from video data and used to determine various aspects of the mental state of an individual portrayed in the video data. Further, the present disclosure provides methods that can be performed using computer-implemented machine learning models to provide real-time analysis of mental state predictions. Advantageously, this allows the mental state predictions to be presented in real-time or substantially real-time, enabling other conversation participants to better understand the individual's mental state as the conversation is occurring. Notably, the real-time mental state predictions enabled by computer-implemented machine learning models enable the systems and methods of the present disclosure to improve accessibility for individuals with hearing, vision, and/or perception impairments. For example, real-time mental state predictions according to the present disclosure can be used to present information conveyed by body language and/or vocal tone to a person with sight and/or hearing impairments, respectively, significantly improving the ability of the person with the impairment or impairments to participate in conversations and other social interactions.

FIG. 1 depicts mental state classification system 10, a system for generating mental state information. Mental state classification system 10 includes mental state classifier 20, which includes processor 22, memory 24, and user interface 26 and is connected to camera devices 28A-N. Camera devices 28A-N capture video data 30A-N of individuals 32A-N. Memory 24 includes video processing module 40, feature extraction module 50, individual mental state prediction module 60, group mental state prediction module 70, and video reconstruction module 76. Memory 24 also stores multidimensional mental state model 80, which includes first dimension 82, second dimension 84, first point 90, second point 92, third point 94, and fourth point 96.

Processor 22 can execute software, applications, and/or programs stored on memory 24. Examples of processor 22 can include one or more of a processor, a microprocessor, a controller, a digital signal processor (DSP), an application specific integrated circuit (ASIC), a field-programmable gate array (FPGA), or other equivalent discrete or integrated logic circuitry. Processor 22 can be entirely or partially mounted on one or more circuit boards.

Memory 24 is configured to store information and, in some examples, can be described as a computer-readable storage medium. Memory 24, in some examples, is described as computer-readable storage media. In some examples, a computer-readable storage medium can include a non-transitory medium. The term "non-transitory" can indicate that the storage medium is not embodied in a carrier wave or a propagated signal. In certain examples, a non-transitory storage medium can store data that can, over time, change (e.g., in RAM or cache). In some examples, memory 24 is a temporary memory. As used herein, a temporary memory refers to a memory having a primary purpose that is not long-term storage. Memory 24, in some examples, is described as volatile memory. As used herein, a volatile memory refers to a memory that that the memory does not maintain stored contents when power to the memory 24 is turned off. Examples of volatile memories can include random access memories (RAM), dynamic random access memories (DRAM), static random access memories (SRAM), and other forms of volatile memories. In some examples, the memory is used to store program instructions for execution by the processor. The memory, in one example, is used by software or applications running on the mental state classifier (e.g., by a computer-implemented machine learning model or a data processing module) to temporarily store information during program execution.

Memory 24, in some examples, also includes one or more computer-readable storage media. The memory can be configured to store larger amounts of information than volatile memory. The memory can further be configured for long-term storage of information. In some examples, the memory includes non-volatile storage elements. Examples of such non-volatile storage elements can include, for example, magnetic hard discs, optical discs, floppy discs, flash memories, or forms of electrically programmable memories (EPROM) or electrically erasable and programmable (EEPROM) memories.

User interface 26 is an input and/or output device and enables an operator to control operation of mental state classifier 20. For example, user interface 26 can be configured to receive inputs from an operator and/or provide outputs regarding predicted mental state. User interface 26 can include one or more of a sound card, a video graphics card, a speaker, a display device (such as a liquid crystal display (LCD), a light emitting diode (LED) display, an organic light emitting diode (OLED) display, etc.), a touchscreen, a keyboard, a mouse, a joystick, or other type of device for facilitating input and/or output of information in a form understandable to users and/or machines.

Mental state classifier 20 is configured to perform one or more methods described herein and/or implement one or more of the mental state classification modules described herein. Mental state classifier 20 can accept data from and/or can be operably connected to an audiovisual data stream and/or an audiovisual data file. Mental state classifier 20 can use data from an audiovisual data stream and/or an audiovisual data file to determine mental state information. More generally, mental state classifier 20 is configured to perform any of the functions attributed herein to a mental state classifier, including receiving an output from any source referenced herein, detecting any condition or event referenced herein, and generating and providing data and information as referenced herein.

Mental state classifier 20 can be a discrete assembly or be formed by one or more devices capable of individually or collectively implementing functionalities and generating and outputting data as discussed herein. In some examples, the mental state classifier can be implemented as a plurality of discrete circuitry subassemblies. In some examples, the mental state classifier can include or be implemented at least in part as a smartphone or tablet, among other options. In some examples, the mental state classifier and/or user interface of the mental state classifier can include and/or be implemented as downloadable software in the form of a mobile application. The mobile application can be implemented on a computing device, such as a personal computer, tablet, or smartphone, among other suitable devices. Mental state classifier 20 can be considered to form a single computing device even when distributed across multiple component devices.

Camera devices 288A-N are capable of capturing video data 30A-N of one or more individuals 32A-N. In the depicted example, camera devices 28A and 28N are depicted as capturing video data 30A and 30N of single individuals 32A and 32N. Camera device 28B is depicted as capturing video data 30B of two individuals 32B and 32C. Each camera device 28A-N captures video data 30A-N of one or more individuals 32A-N. Each camera device 28A-N is configured to be able to communicate with mental state classifier 20 and mental state classifier 20 is configured to communicate with each camera device 28A-N. Camera devices 28A-N can be, for example, a video camera, a webcam, or another suitable source for obtaining video data 30A-N. Camera devices 28A-N can be controlled by mental state classifier 20 or by another suitable video device. Video data 30A-N are audiovisual data feeds portraying individuals 32A-N. Video data 30A-N can be stored to memory 24 for use with one or more methods described herein or can be stored to another storage media and recalled to memory 24 for use with one or more methods described herein.

Although mental state classification system 10 is depicted as only including three camera devices 28A-N, mental state classification system 10 can include any number of camera devices 28A-N. Each additional camera device 28A-N can capture video data 30A-N portraying another individual 110A-N. Similarly, although each of video data 30A-N is depicted as portraying a single individual 110A-N, in other examples each of video data 30A-N can depict two or more individuals 110A-N.

Video processing module 40 includes one or more programs for processing video data 30A-N. For example, video processing module 40 can include one or more programs for extracting image data, audio data, and semantic text data from video data 30A-N. As used herein, "image data" refers to the portion of video data 30A-N that is a series of still images, "audio data" refers to the sound data stored in video data 30A-N, and semantic text data refers to data that represents spoken words, phrases, sentences, and other sounds produced by an individual as readable text.

Feature extraction module 50 includes one or more programs for classifying the image data, audio data, and semantic text data extracted by video processing module 40. Feature extraction module 50 can include one or more programs for extracting classifiable features from the image data, audio data, and/or semantic text data. In some examples, feature extraction module 50 can include one or more computer-implemented machine learning models for extracting classifiable features from the image data, audio data, and/or semantic text data. The features extracted by feature extraction module 50 are capable of being classified to predict an individual's mental state and/or to identify the individual.

Individual mental state prediction module 60 includes one or more programs for predicting the mental state of one or more individuals portrayed in video data 110A-N based on the features extracted by feature extraction module 50. In some examples, individual mental state prediction module 60 can use one or more computer-implemented machine learning models to predict the mental state of an individual portrayed in video data.

Group mental state prediction module 70 includes one or more programs for predicting the mental state of a group of one or more individuals for which individual mental states were predicted using individual mental state prediction module 60. In some examples, group mental state prediction module 70 can use one or more computer-implemented machine learning models to predict the mental state of a group portrayed in video data.

In operation, mental state classifier 20 can use programs of individual mental state prediction module 60 and group mental state prediction module 70 to determine the mental state for all individual within a group and to subsequently determine an overall group mental state for the group of individuals. One method of determining an overall group mental state performable by individual mental state prediction module 60 and group mental state prediction module 70 is described subsequently with respect to FIG. 2.

Outlier identification module 72 includes one or more outliers among the individual mental states predicted by individual mental state prediction module 60. More specifically, outlier identification module 72 includes one or more programs that can compare individual mental states predicted by individual mental state prediction module 60 with a group mental state predicted by group mental state prediction module 70 to determine whether any of the individual mental states differ from the group mental state by a threshold amount.

Video reconstruction module 76 includes one or more programs for reconstructing enhanced video data. The enhanced video data includes the image data and audio data extracted from the video data processed by video processing module 40, but is enhanced with additional images, audio, and/or text based on the information generated by individual mental state prediction module 60 and/or group mental state prediction module 70. The enhanced video produced by video reconstruction module 76 can be output by user interface 26 to enable a user to quickly understand the information generated by individual mental state prediction module 60 and/or group mental state prediction module 70 while watching only video feed of the individual and/or group.

Memory 24 also stores multidimensional mental state model 80, which is a model for classifying the mental state of an individual 32A-N portrayed in video data 30A-N. Multidimensional mental state model 80 includes first dimension 82 and second dimension 84. As used herein, a "multidimensional mental state model" refers to a model of mental state that assigns different aspects of mental state to different dimensions of the model. Advantageously, the use of multidimensional mental state models significantly improves the resolution and accuracy of mental state predictions as compared to existing models of mental state, which use, at most, a single dimension to distinguish between different mental states. Many existing methods of analyzing mental state attempt to identify mental state based only on the presence or absence of features associated with a particular mental state. Where a model is used to analyze mental state, existing methods use a model that contains at most a single dimension, with different mental states ordered along the single dimension of mental state. Advantageously, the use of a multidimensional mental state model allows for significant improvements in resolution between similar mental states, which significantly improves the accuracy of mental state predictions made using the multidimensional mental state model.

Referring to multidimensional mental state model 80, first dimension 82 can represent an intensity of an individual's mental state and second dimension 84 can represent a pleasantness of the individual's mental state. Different mental states can be described by different combinations of values in first dimension 82 and second dimension 84. For example, each quadrant of multidimensional mental state model 80 can represent a different mental state or different subregions of multidimensional mental state model 80 (including subregions entirely within and/or extending across quadrants of multidimensional mental state model 80) can represent different mental states.

Points 90-96 represent different combinations of values along the first dimension and the second dimension of multidimensional mental state model 80. In examples where first dimension 82 and second dimension 84 represent intensity and pleasantness of an individual's mental state, respectively, point 90 corresponds to a mental state having relatively high intensity and relatively high pleasantness, such as happiness. Point 92 corresponds to a mental state having relatively high intensity and relatively low pleasantness, such as frustration or annoyance. Point 94 corresponds to a mental state having low intensity and low pleasantness, such as boredom. Point 96 corresponds to a mental state having low intensity and high pleasantness, such as relaxation.

Additionally and/or alternatively, the dimensions of multidimensional mental state model 80 can represent mental state by describing aspects of information communicated by the individual (i.e., in the image data, audio data, and/or semantic text data for an individual), such as the relative importance of the information the individual is conveying information, the positivity of the information the individual is conveying, and/or the subject of the conversation in which the individual is participating (e.g., whether the subject is administrative, technical, etc.), among other options. The importance of the information the individual is conveying can be assessed based on, for example, a task or job the individual is performing. In these examples, multidimensional mental state models, such as multidimensional mental state model 80, more accurately describe the mental state of an individual than mental state models having only a single dimension. For example, multidimensional mental state model 80 enables the mental states of amusement, excitement, happiness, delight, gladness and pleasure to be distinguished. Existing, one-dimensional models of mental state are unable to clearly distinguish between closely related mental states.

In other examples, each of first dimension 82 and second dimension 84 can represent separate mental states. For example, first dimension 82 can represent a first mental state, such as confusion, and second dimension 84 can represent a second mental state, such as calmness. Various regions, such as quadrants, of multidimensional mental state model 80 can represent different combinations of confusion and calmness, with each region representing a discrete overall mental state. In these examples, multidimensional mental state models also provide a more accurate descriptions of mental state than models that only describe a single mental state. For example, it is possible for an individual to simultaneously experience both boredom and confusion. A two-dimensional mental state model can provide nuanced information about the intensity with which an individual is experience boredom and confusion, allowing for sophisticated predictions of the individual's overall mental state. For example, a combination of high boredom and high confusion may indicate that an individual is inattentive because of a lack of understanding, while a combination of high boredom and low confusion may indicate that the individual is inattentive because of a lack of stimulation and/or intellectual challenge.

In other examples, the dimensions of multidimensional mental state model 80 can represent any other combination of mental states. For example, the dimensions of multidimensional mental state model can be one or more of tiredness, sleepiness, serenity, satisfaction, calmness, relaxation, contentment, distress, frustration, anger, annoyance, tension, fear, alarm, misery, sadness, depression, gloom, boredom, astonishment, amusement, excitement, happiness, delight, gladness, pleasure, thankfulness, gratitude, confusion, smugness, deliberation, anticipation, cheer, sympathy, trust, humor, envy, melancholy, hostility, resentment, revulsion, and/or ennui.

Further, multidimensional mental state models having more than two dimensions more accurately describe the mental state of an individual than mental state models having only two dimensions. For example, it is possible for an individual to be confused, envious, and sleepy simultaneously, with various combination of each mental state indicating a different overall mental state. A three-dimensional mental state model having dimensions describing each of confusion, envy, and sleepiness can more accurately describe the mental state of an individual experiencing all three mental states to varying degrees than existing representations or models of mental state.

Individual mental state prediction module 60 can be used to generate values for each dimension of multidimensional mental state model 80 for each individual. Similarly, group mental state prediction module 70 can be used to generate values for each dimension of multidimensional mental state model 80 for the group of individuals. In some examples, individual mental state prediction module 60 and/or group mental state prediction module 70 can use different types of data (i.e., image, audio, and semantic text) can be used to generate values for each of first dimension 82 and second dimension 84. The use of different combinations of the three types of information present in video data provides further advantages and improvements to both the efficiency and accuracy of the multidimensional mental state model. More specifically, excluding different combinations of image, audio, and text data allows mental state predictions to be made using only predictive data rather than non-predictive data. For example, text data may offer significantly more insight into the importance of a particular discussion than image or audio data. The multidimensional mental state model can be configured so that only features from the text data are used to calculate the dimension associated with discussion importance, improving accuracy by disregarding non-predictive data and, consequently, improving efficiency by only requiring one type of data to calculate the dimensional value for the discussion importance dimension.

While multidimensional mental state model 80 is depicted in FIG. 1 as only including first dimension 82 and second dimension 84, additional dimensions can be added to multidimensional mental state model 80 as required for a given application and/or operational need. Adding additional dimensions to multidimensional mental state model 80 can allow nearby or similar mental states to be further distinguished, thereby improving the resolution of multidimensional mental state model 80. For example, additional dimensions describing information importance, information positivity, the subject of the information (i.e., whether the information is administrative, technical, etc.), and/or other mental states can further be used to resolve and distinguish between similar overall mental states.

In operation, mental state classifier 20 allows for the prediction of mental state based only on information communicated by an individual 32A-N in video data 30A-N captured by cameras 28A-N. Conventional methods of predicting mental state rely on complex biometric data. Collecting biometric data can require complex machines and, further, often requires physically-intrusive methods. Conversely, mental state classifier 20 allows for mental state to be predicted using only video data 30A-N, which can be collected using only cameras 28A-N and without the use of any physically-intrusive techniques.

Figure 2:
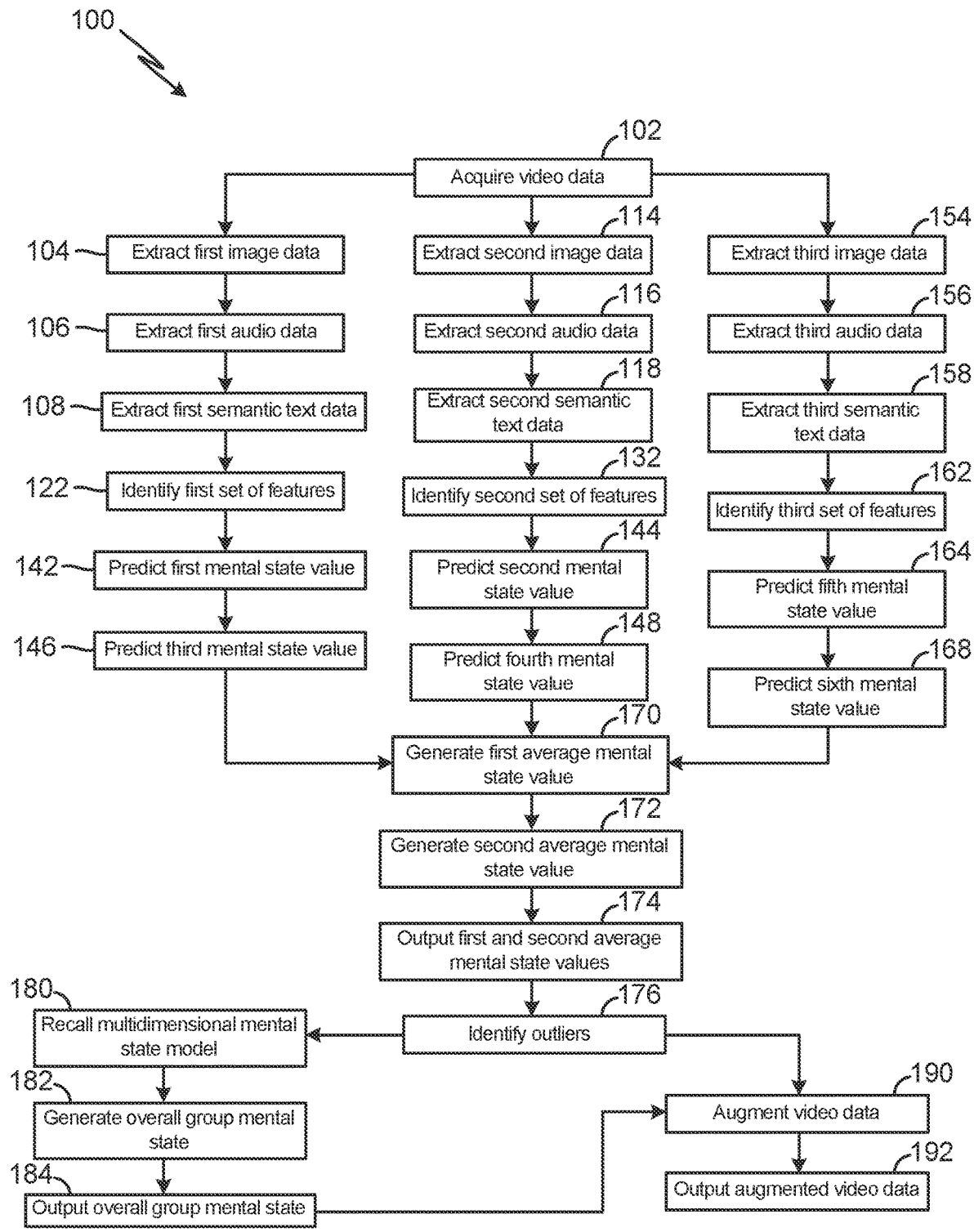
FIG. 2 is a flow diagram of an example of a method of predicting a group mental state.

FIG. 2 depicts method 100, which is a method of determining a group mental state. Method 100 includes steps 102-192 of acquiring video data (step 102), extracting first image data (step 104), extracting first audio data (step 106), extracting first semantic text data (step 108), extracting second image data (step 114), extracting second audio data (step 116), extracting second semantic text data (step 118), identifying a first set of features (step 122), identifying a second set of features (step 132), predicting a first mental state value (step 142), predicting a second mental state value (step 146), predicting a third mental state value (step 148), predicting a fourth mental state value (step 150), extracting third image data (step 154), extracting third audio data (step 156), extracting third semantic text data (step 158), identifying a third set of features (step 162), predicting a fifth mental state value (step 164), predicting a sixth mental state value (step 168), generating a first average mental state value (step 170), generating a second average mental state value (step 172), outputting the first and second average mental state values (step 174), identifying outliers (step 176), recalling a multidimensional mental state model (step 182), generating an overall group mental state (step 184), outputting the overall group mental state (step 186), creating augmented video data (step 190), and outputting the augmented video data (step 192). Method 100 can be stored to memory 24 of mental state classifier 20 and executed by processor 22. For explanatory purposes, method 100 will generally be described herein with reference to mental state classifier 20. However, method 100 can also be performed by any other suitable device or system.

As will be explained in more detail subsequently, method 100 allows for the prediction of a group mental state based on a first average mental state value and a second average mental state value. While it is possible to determine mental state values for each individual in a group, it can be difficult for an individual interacting with the group to comprehend and act on individualized mental state information while interacting with the group, especially where the group is large. Further, it can be difficult for an individual interacting with the group to quickly and accurately generate an "average" or "overall" mental state based on a large dataset of individual mental state values. It can be similarly difficult for members of a group to fully understand the mental state of the other individuals in the group, and the advantages of method 100 outlined with respect to individuals interacting with the group also apply examples where method 100 is used by members of a group to understand group mental state. Further, existing methods do not allow for the determination of complex mental states for a group. Method 100 advantageously allows for determination of complex mental states having multiple components. Advantageously, method 100 allows for the determination of average mental state information for a group, including information describing complex mental states.

In step 102, video data is acquired. The video data can be any media source having both audio and image components. The video data can be delivered to mental state classifier 20 from a video source and/or mental state classifier 20 can request the video data from the video source. The video source can be any suitable source of video, such as a multimedia file or a video stream. The video data can be of any length, but in some examples, the video data is sampled at pre-determined intervals for use with method 100. Method 100 can be performed for each segment of the video data and updated mental state information can be provided for each segment.

The video data acquired in step 102 contains all individuals of a group for which a group mental state is desired. The video data acquired in step 102 contains footage of at least two individuals. In some examples, the video data in step 102 can contain footage of three or more individuals. As will be explained in more detail subsequently, where the video data acquired in step 102 contains only two individuals, steps 154-168 can be omitted. Where the video data acquired in step 102 contains four or more individuals, steps 154-168 can be repeated the fourth individual and for each additional individual over four, as will also be explained in more detail subsequently.

The video data acquired in step 102 can be acquired by one or more cameras, where each camera captures video of at least one individual. The video data acquired in step 102 can, for example, one or more of video data 30A-N and be taken by a single camera 28A-N or can be taken by multiple cameras 28A-N. Each camera can capture one or more individuals. In some examples, all individuals of the group can be captured by a single camera (e.g., one of cameras 28A-N) and the video data captured by the camera can be used as the video data acquired in step 102. In other examples, all individuals of the group can be captured by multiple cameras and the video data captured by those cameras can be compiled and/or aggregated to form the video data acquired in step 102.

In step 104, first image data is extracted from the video data acquired in step 102. The first image data is stored to memory 24 as a series of still images for use with later steps of method 100 and depicts only a first individual of the group. The first image data can be extracted by processor 22 of mental state classifier 20 (FIG. 1) with one or more programs of video processing module 40. Where the video data that portrays the first individual also includes other individuals, such that the video data of the first individual is non-separable from the video data of the other individuals, the image data extracted from that video data can be cropped to only include the first individual. Processor 22 can identify an individual from the still image data and crop each image of the still image data to include only that individual. The still image data can include one image for each frame of the video data or can be sampled at a pre-determined rate. For example, the video data can be sampled once every three frames to generate the still image data.

In some examples, the still image data derived from the video data may contain images in which the first individual is not present. In these examples, the still image data can be trimmed to include only images in which the first individual is present. The trimmed, cropped image data can then be stored to memory 24 as the first image data.

In step 106, first audio data is extracted from the video data. The extracted audio data is stored to memory 24 for use with later steps of method 100 and includes only audio of the first individual. The first audio data can be extracted by processor 22 of mental state classifier 20 (FIG. 1) with one or more programs of video processing module 40. Where the video data that portrays the first individual also includes other individuals, the audio data extracted from that video data can be trimmed to include audio of only the first individual. The trimmed audio is stored to memory 24 as the first audio data. The audio can be trimmed by, for example, diarizing the audio file to separate the audio extracted from the video data into multiple audio files corresponding to each individual in the group.

In some examples, processor 22 can execute one or more programs stored on memory 24 to identify which portions of the audio data in which an individual is communicating and trim the audio data to include only those portions. Trimming the audio data can reduce the file size of the audio data, which can improve the ease with which steps 122, 142, and/or 146 can be performed in some examples. The program can be, for example, a computer-implemented machine learning model trained to identify individuals based on voices present in audio data.

Where the video data of the first individual also includes other individuals, such that the video data of the first individual is non-separable from the video data of the other individuals, processor 22 can use one or more programs stored to memory 24 to determine which portions of the audio correspond to the first individual identified in the image data. Processor 22 (FIG. 1) can determine which portions of the audio correspond to the first individual by, for example, inspecting metadata of the video data acquired in step 202. Additionally and/or alternatively, processor 22 can execute one or more programs to identify individuals present in the image data and individuals present in the audio data. The processor 22 can cross-reference a library of individuals to determine which diarized or trimmed audio files correspond to the first individual and store those audio files as the first audio data. Additionally and/or alternatively, the processor 22 can execute one or more programs to analyze the first image data and determine when the first individual is talking. The processor 22 can then use that timestamp information to determine which portions of the audio file correspond to the first individual and store those portions of the audio as the first audio data.

In step 108, the first semantic text data is extracted. As referred to herein, "semantic text data" refers to data that represents spoken words, phrases, sentences, and other sounds produced by the first individual as readable text. The semantic text data can be, for example, a transcript of the words spoken in the audio portion of the video data. The first semantic text data can be extracted from, for example, the first audio data extracted in step 106. Processor 22 of mental state classifier 20 (FIG. 1) can use one or more programs of video processing module 40 to extract the first semantic text data. The semantic text data can be extracted from the audio data using a text-to-speech program or another suitable tool and can be stored as the first semantic text data. In other examples, the video data can include a semantic text transcript of words, phrases, sentences, etc. spoken by the individual, and the first semantic text data can be extracted directly from the video data. In these examples, the semantic text data can be correlated to the correct individual in the group by, for example, comparing timestamp information to the image and audio data, by comparing the semantic text data extracted from the video data to partial semantic text information derived from an extracted audio data set, or by another suitable method.

In step 114, second image data is extracted from the video data. The second image data can be extracted in substantially the same way as described previously with respect to the extraction of the first image data in step 104, but the second image data contains only still images of a second individual present in the video data. In some examples, the second image data can be extracted using the uncropped still image data extracted in step 104. In other examples, the second image data can be extracted by first extracting new uncropped still image data from the video data acquired in step 102 and then cropping the new uncropped still image data to only include still images of the second individual.

In step 116, second audio data is extracted from the video data. The second audio data can be extracted in substantially the same way as described previously with respect to the extraction of the first audio data in step 106. However, the second audio data contains only diarized or trimmed audio of the second individual.

In step 118, second semantic text data is extracted. The second semantic text data can be extracted in substantially the same way as described previously as with respect to the extraction of the first semantic text data in step 108, but contains only semantic text of the second individual.

In step 122, a first set of features is identified. The first set of features are identified from one or more of the first image data extracted in step 104, the first audio data extracted in step 106, and the first semantic text data extracted in step 108. The first set of features are classifiable features of the first individual and can be used to determine aspects of the mental state of the first individual in subsequent steps 142 and 146. Processor 22 of mental state classifier 20 (FIG. 1) can use one or more programs of feature extraction module 50 to identify the first set of features and store those features to memory 24 for use with subsequent steps of method 100. More specifically, processor 22 can inspect and identify features from one or more of the first image data, the first audio data, and the first semantic text data. The first image data, the first audio data, the first semantic text data, or any combination thereof can be selected to generate the first set of features in step 122 based on application or operational need or based on the mental state values determined in subsequent steps 142 and/or 146. For example, if the group depicted in the video data is unlikely to be talking, the first set of features in step 122 can be identified from only the image data. As a further example, where one or more of image data, audio data, and/or semantic text data are not predictive of the mental state value generated in steps 142 and/or 146, the corresponding data of the first image data, first audio data, and first semantic text data can be omitted from the first set of features. Where one or more of the image data, audio data, and/or semantic text data are omitted from the first set of features, the corresponding step or steps of steps 104-108 can also be omitted from method 100.

Each type of data can be inspected using one or more software tools to identify features that can be stored as features of the first set of features. The first image data can be analyzed using, for example, a computer vison model or another machine learning model to identify one or more body language elements that can be stored as features of the first set of features. The body language elements can include, for example, one or more of hand gestures, head tilt, the presence and amount of eye contact, the amount of eye blinking, forehead wrinkling, mouth position, mouth shape, eyebrow shape, and/or eyebrow position. The first audio data can be analyzed using, for example, one or more computer-implemented machine learning models to identify features related to information conveyance. For example, the features identified from the audio data can be one or more of a vocal tone, a vocal cadence, a vocal pitch, the presence of vocal quavering, intonation, inflection, sentences stress, or another audio element indicative of information conveyance. The first semantic text data can be analyzed using, for example, a natural language understanding model or another machine learning model. The features can be, for example, phonemes, words, phrases, sentences, or other units of language that convey information and are stored in the semantic text data. The features can also be, for example, an intent and/or an entity in the semantic text data. A classifiable intent can include, for example, the intended meaning of a semantic text phrase. A classifiable entity can include, for example, words, phrases, sentences, or other units of language that provide additional context to further describe or classify an intent. In some examples, the model can compare the semantic text transcript of the individual to a library of vectorized text data to determine the content of the semantic text data.

Once features have been identified from the first image data, the first audio data, and/or the first semantic text data, the features can be stored as the first set of features for use with subsequent steps of methods 100. The features of the first set of features can be stored to, for example, memory 24.

In step 132, a second set of features is identified. The second set of features is based on one or more of the second image data extracted in step 114, the second audio data extracted in step 116, and the second semantic text data extracted in step 118. The second set of features are classifiable features of the second individual and can be used to determine aspects of the mental state of the second individual in subsequent steps 144 and 148. Whether the second image data, the second audio data, the second semantic text data, or a combination thereof is used to create the second set of features can be determined in substantially the same way as described previously with respect to the first set of features identified in step 122. Further, features for the second set of features can be identified from each of the second image data, the second audio data, and the second semantic text data in substantially the same manner as described previously with respect to the first set of features identified in step 122.

Steps 142-148 relate to the creation of four mental state values. As will be explained in more detail the first and third mental state values describe mental states of the first individual and the second and fourth mental state values describe mental states of the second individual. Processor 22 of mental state classifier 20 (FIG. 1) can perform each of steps 142-148 with one or more programs of individual mental state prediction module 60. As will also be explained in more detail subsequently, the first and second mental state values describe a first mental state and the third and fourth values describe a second mental state. The first and second mental states are different, allowing resolution of each individual's mental state to be resolved in two dimensions, the advantages of which will be described in more detail subsequently.

In step 142, a first mental state value is predicted. The first mental state value describes a first mental state of the first individual using alphanumeric characters and is predicted based on the features stored in the first set of features. The first mental state value can be a numeric representation of, for example, an intensity of a mental state. The first mental state value can also represent, for example, a number of features associated with the first mental state that are present in the first set of features. The first mental state value can be predicted using, for example, a computer-implemented machine learning algorithm trained to identify features corresponding to the first mental state. The first mental state value can be predicted using, for example, processor 22 and can be stored to, for example, memory 24 for use with subsequent steps of method 100.

In step 144, a second mental state value is predicted. The second mental state describes the same mental state as the first mental state value but describes that first mental state with respect to the second individual. The second mental state value is stored as alphanumeric characters and is predicted based on the features stored in the second set of features. The second mental state value represents the first mental state in substantially the same manner as the first mental state value. For example, if the first mental state value describes an intensity of the first mental state, the second mental state value also describes an intensity of the first mental state. Similarly, if the first mental state value describes a number of features associated with the first mental state that are present in the first set of features, the second mental state value can describe a number of features associated with the first mental state that are present in the second set of features. The second mental state value can be predicted using, for example, the same computer-implemented machine learning algorithm used to predict the first mental state value. The second mental state value can also be predicted using processor 22 of mental state classifier 20 (FIG. 1) and can be stored to memory 24 for use with subsequent steps of method 100.

In step 146, a third mental state value is predicted. The third mental state value describes a second mental state of the first individual using alphanumeric characters and is predicted based on the features stored in the first set of features. The third mental state value can be a numeric representation of, for example, an intensity of the second mental state. The third mental state value can also represent, for example, a number of features associated with the second mental state that are present in the first set of features. The third mental state value can be predicted using, for example, a computer-implemented machine learning algorithm trained to identify features corresponding to the second mental state. The third mental state value can be predicted using, for example, processor 22 (FIG. 1) and can be stored to, for example, memory 24 for use with subsequent steps of method 100.

In step 148, a fourth mental state value is predicted. The fourth mental state describes the same mental state as the third mental state value but describes that second mental state with respect to the second individual. The fourth mental state value is stored as alphanumeric characters and is predicted based on the features stored in the second set of features. The fourth mental state value represents the second mental state in substantially the same manner as the third mental state value. For example, if the third mental state value describes an intensity of the second mental state, the fourth mental state value also describes an intensity of the first mental state. Similarly, if the third mental state value describes a number of features associated with the second mental state that are present in the first set of features, the fourth mental state value can describe a number of features associated with the second mental state that are present in the second set of features. The fourth mental state value can be predicted using, for example, the same computer-implemented machine learning algorithm used to predict the third mental state value. The fourth mental state value can also be predicted using processor 22 (FIG. 1) and can be stored to memory 24 for use with subsequent steps of method 100.

As described previously, the first and second mental states are different mental states, such that method 100 simultaneously allows for the prediction of multiple mental state components for each individual captured in the video data. Predicting multiple mental state components for each individual allows for more detailed information can provide significantly more information than predictions that rely on singular mental state determinations, especially where the first and second mental states are not related. For example, the first mental state can be confusion and the second mental state can be calmness. Method 100 allows for quantitative prediction of the overall level of confusion for each individual and simultaneously allows for the quantitative prediction of the overall level of calmness for each individual. Simultaneously monitoring confusion and calmness can allow, for example, a measurement of how well the first individual and the second individual are retaining information as audience members to a presentation or lecture. More specifically, high confusion and low calmness can both indicate a low degree of information retention. A presenter or lecturer can act on each dimension of the first and second individuals' mental states to increase information retention according to the information predicted using method 100. That is, the presenter or lecturer can adopt different strategies to increase audience calmness and to decrease confusion, and the information provided by method 100 can indicate to the presenter or lecturer which aspect of audience mental state should be targeted to increase information retention. Other combinations of mental states are possible and can be chosen based on application or operational need. For example, the mental states can be a combination of any of tiredness, sleepiness, serenity, satisfaction, calmness, relaxation, contentment, distress, frustration, anger, annoyance, tension, fear, alarm, misery, sadness, depression, gloom, boredom, astonishment, amusement, excitement, happiness, delight, gladness, pleasure, thankfulness, gratitude, confusion, smugness, deliberation, anticipation, cheer, sympathy, trust, humor, envy, melancholy, hostility, resentment, revulsion, and/or ennui.

As the first and second mental state values describe the same mental state in the same manner, the first mental state value and the second mental state value can be directly compared, and information can be determined based on the comparison. Similarly, as the third and fourth mental state values also describe the same mental state in the same manner, the third mental state value and the fourth mental state value can be directly compared, and information can be determined based on that comparison. For example, the first and second mental state values and/or third and fourth mental state values can be compared against a pre-determined ideal value to understand how the first and second individuals are experiencing the first mental state. The result of the comparison can be output to user interface 26 for use by a user interacting with the group including the first and second individuals. As a further example, the first and second mental state values can also be compared to determine if they differ by more than a pre-determined threshold value. If the first and second mental state values differ by more than a threshold value, a message and/or icon can be output to user interface 26.

Notably, however, as the first mental state and second mental states are different, the first and second mental state values are not required to describe the first mental state in the same or in substantially the same manner as the third and fourth mental state values describe the second mental state. For example, the first and second mental state values can describe an intensity of the first mental state and the third and fourth mental state values can describe a number of features associated with the second mental state present in the first and second sets of features, respectively.

For some applications, it may be advantageous to evaluate more than two aspects of each individual's mental state. In these examples, steps 142, 144 and 146, 148 can be repeated to create mental state values for each individual for each additional mental state with separately-trained computer-implemented machine learning models. Any number of additional mental state values can be produced in substantially the same manner as outlined previously with respect to steps 142, 144 and 146, 148. Notably, the use of additional mental state values provides further information describing and distinguishing each individual's mental state.

Where the video data contains three individuals, method 100 can optionally include steps 154-168 to generate mental state values for the third individual. In step 154, third image data of a third individual is extracted from the video data. The third image data can be extracted in substantially the same way as described previously with respect to the extraction of the first image data in step 104 and the second image data in step 114, but the third image data contains only still images of the third individual present in the video data.

In step 156, third audio data is extracted from the video data. The third audio data can be extracted in substantially the same way as described previously with respect to the extraction of the first audio data in step 106 and the second audio data in step 116. However, the third audio data contains only diarized or trimmed audio of the third individual.

In step 158, third semantic text data is extracted. The third semantic text data can be extracted in substantially the same way as described previously as with respect to the extraction of the first semantic text data in step 108 and the extraction of the second semantic text data in step 118. The third semantic text data can be extracted from the third audio data and/or the video data, and represents utterances made by the third individual.

In step 162, a third set of features is identified. The third set of features is based on one or more of the third image data extracted in step 154, the third audio data extracted in step 156, and the third semantic text data extracted in step 158. The third set of features are classifiable features of the third individual and can be used to determine aspects of the mental state of the second individual in subsequent steps 164 and 168. Whether the third image data, the third audio data, the third semantic text data, or a combination thereof is used to create the third set of features can be determined in substantially the same way as described previously with respect to the first set of features identified in step 122 and/or the second set of features identified in step 132. Further, features for the third set of features can be identified from each of the third image data, the third audio data, and the third semantic text data in substantially the same manner as described previously with respect to the first set of features identified in step 122 and/or the second set of features identified in step 132.

In step 164, a fifth mental state value is predicted. The first mental state describes the same mental state as the first mental state value and the second mental state value but describes that mental state with respect to the third individual. The fifth mental state value is stored as alphanumeric characters and is predicted based on the features stored in the third set of features. The fifth mental state value represents the first mental state in substantially the same manner as the first mental state value predicted in step 142 and the second mental state value predicted in step 144. For example, if the first and second mental state values describe an intensity of the first mental state, the fifth mental state value also describes an intensity of the first mental state. Similarly, if the first and second mental state values describe a number of features associated with the first mental state that are present in the first and second sets of features, respectively, the fifth mental state value can describe a number of features associated with the first mental state that are present in the second set of features. The fifth mental state value can be predicted using, for example, the same computer-implemented machine learning algorithm used to predict the first and second mental state values. The fifth mental state value can also be predicted using processor 22 of mental state classifier 20 (FIG. 1) and can be stored to memory 24 for use with subsequent steps of method 100. Processor 22 can use one or more programs of individual mental state prediction module 60 to generate the fifth mental state value.

In step 168, a sixth mental state value is predicted. The sixth mental state describes the same second mental state as the third mental state value and the fourth mental state value but describes that second mental state with respect to the third individual. The sixth mental state value is stored as alphanumeric characters and is predicted based on the features stored in the third set of features. The sixth mental state value represents the first mental state in substantially the same manner as the third and fourth mental state values. For example, if the third and fourth mental state values describe an intensity of the second mental state, the sixth mental state value also describes an intensity of the second mental state. Similarly, if the third and fourth mental state values describe a number of features associated with the second mental state that are present in the first and second sets of features, respectively, the sixth mental state value can describe a number of features associated with the second mental state that are present in the third set of features. The sixth mental state value can be predicted using, for example, the same computer-implemented machine learning algorithm used to predict the third and fourth mental state values. The sixth mental state value can also be predicted using processor 22 (FIG. 1) and can be stored to memory 24 for use with subsequent steps of method 100. Processor 22 can use one or more programs of individual mental state prediction module 60 to generate the sixth mental state value.

As the fifth mental state value describes the first mental state in the same or substantially the same way as the first and second mental state values, the first, second, and fifth mental state values can be directly compared, and information can be determined based on the comparison. Similarly, as the sixth mental state value describes the second mental state in the same or substantially the same way as the third and fourth mental state values, the third, fourth, and fifth mental state values can be directly compared, and information can be determined based on the comparison.

Where the video data acquired in step 102 includes more than three individuals, steps 104-146, 114-148, 154-168 can be repeated for each individual over three, allowing method 100 can be expanded to generate mental state values for all individuals in a group of any size. The additional individual mental state values can be used, in turn, to predict the group mental state.

Figure 3:
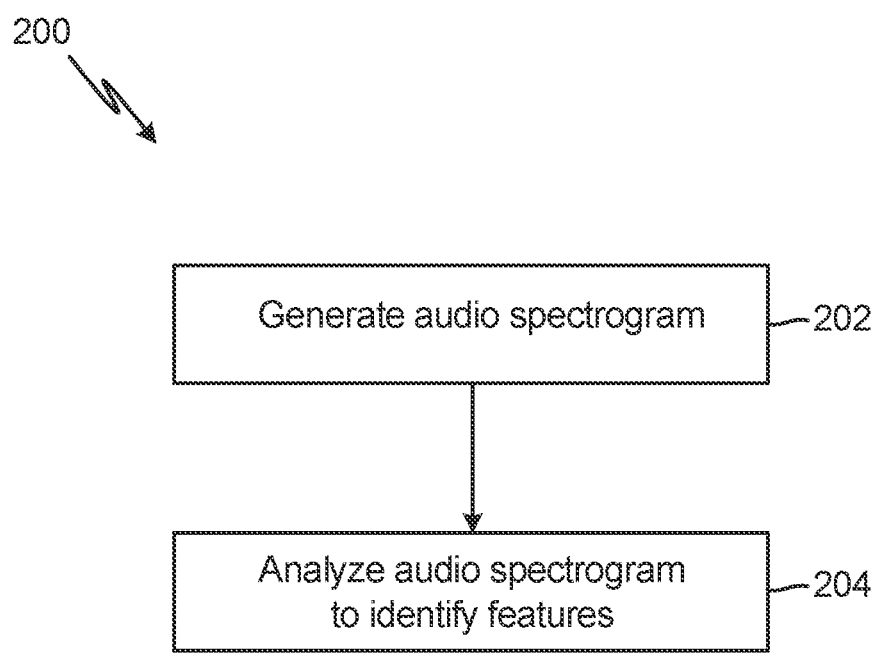
FIG. 3 is a flow diagram of an example of a method of identifying features in audio data suitable for use with the method of FIG. 2.

In some examples, the audio data can be converted to an audio spectrogram and that can be analyzed in steps 122, 132, and/or 162 to identify features for the first, second, and/or third feature sets. FIG. 3 is a flow diagram of method 200, which is a method of analyzing audio data that can be performed during steps 122, 132, and/or 162 of method 100. Method 200 includes steps 202-204 of generating an audio spectrogram (step 202) and analyzing the audio spectrogram to identify features for the second feature set (step 204).

In step 202, the audio data extracted in steps 106, 116, and/or 156 is converted to a spectrogram. The spectrogram can describe, for example, the amplitude or frequency ranges of the audio data. In step 204, features present in the audio spectrogram are identified for inclusion in the first, second, and/or third feature sets. In some examples, processing the audio data as an audio spectrogram enables control circuitry and/or a processor performing steps 122, 132, and/or 162 (e.g., processor 22 of mental state classifier 20) to more easily identify features in the audio data.

Returning to method 100, steps 170-176 relate to the creation of average mental state values and the identification of outliers within the group. Steps 170-176 can be performed for a group having any number of individuals, but steps 170-176 will be discussed with respect to a group of three individuals for explanatory purposes.

In step 170, a first average mental state value is generated. The first average mental state value is generated by averaging the first mental state value, the second mental state value, and the fifth mental state value. As such, the first average mental state value represents an average of the first mental state for the group. The first average mental state value can be generated using, for example, processor 22 (FIG. 1) and can be stored to, for example, memory 24 of mental state classifier 20. Processor 22 can use one or more programs of group mental state prediction module 70 to perform step 170.

In step 172, a second average mental state value is generated. The first average mental state value is generated by averaging the third mental state value, the fourth mental state value, and the sixth mental state value. As such, the second average mental state value represents an average of the second mental state for the group. The second average mental state can be generated using, for example, processor 22 (FIG. 1) and can be stored to, for example, memory 24 of mental state classifier 20. Processor 22 can use one or more programs of group mental state prediction module 70 to perform step 172.

In step 174, the first and second average mental state values are output. The first and second average mental state values can be output to, for example, user interface 26 of mental state classifier 20. The average mental state values can be output as, for example, one or more words, symbols, and/or icons. Additionally and/or alternatively, the average mental state values can be output as audio describing the average mental state values.

An individual interacting with the group can use the average mental state values to quickly ascertain the overall mental state of the group. Notably, it can be cognitively difficult for an individual interacting with the group to comprehend and act on individual mental state scores for two mental states of all individuals in the group while the interacting individual simultaneously attempts to engage with the group and perform group interaction skills at an adequate level. Using a lecturer as a specific example, it can be difficult to track mental state scores of two mental states for all members in the audience while simultaneously recalling all information required for the lecture, reviewing lecture notes, and engagingly delivering a lecture.

Advantageously, the average first and second mental state values output in step 174 significantly simplify the mental state information presented to an individual interacting with the group, thereby reducing the cognitive load required to understand audience mental state. Reducing the cognitive load required to understand audience mental state can improve the ability of an individual interacting with the group to act on mental state information created using method 100. Moreover, reducing cognitive loads required to understand audience mental state can also improve the ability of the individual to perform group interaction skills as compared to methods that do not create average mental state values by freeing cognitive capacity for those group interaction skills.

The cognitive difficulties in understanding individual group mental state scores can be particularly pronounced for large groups. For example, it can be significantly more difficult to comprehend mental state scores for an audience of 100 people than for an audience of 5 people. As described previously, method 100 can be scaled to cover an audience of any size, and steps 170-174 can be used to create average group mental state values based on any number of individual mental state values. As such, method 100 offers further advantages over existing methods by allowing the estimation of average mental state for groups of any size, including large groups.

The average group mental state values produced in steps 170-172 can also be output to individual group members, improving the ability of group members to track the mental state of other members of the group. For the same reasons as outlined previously with respect to individuals interacting with a group, it can also be cognitively burdensome to track the mental state for a group member to track the mental state of all other group members. For example, a group leader may need to simultaneously ingest information while ensuring that other group members are ingesting the same information. Advantageously, method 100 reduces the mental states of all other group members to average values, significantly freeing cognitive capacity of the group leader to focus on information ingest.

Figure 4:
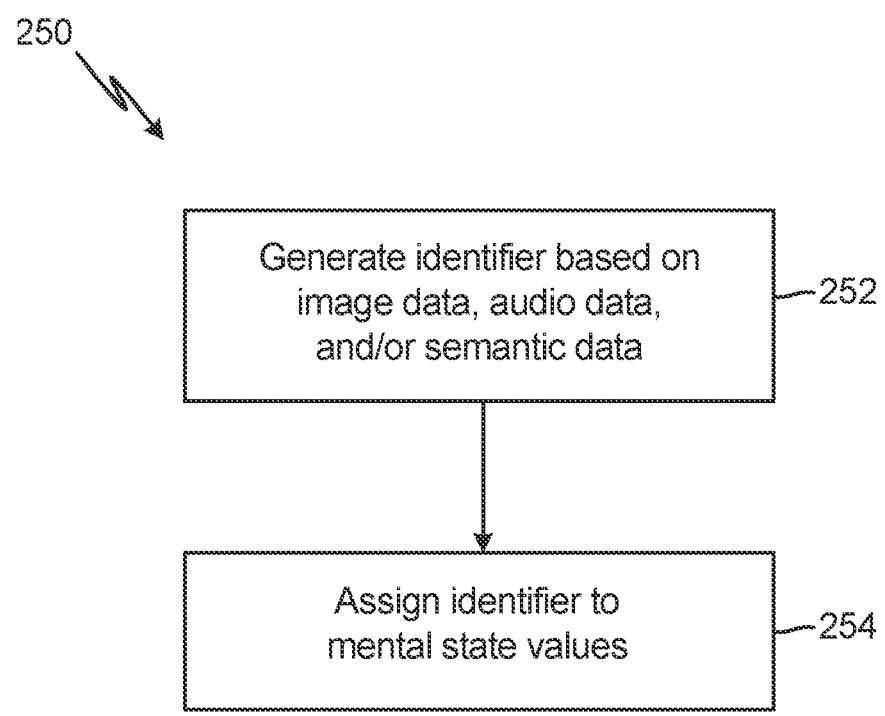
FIG. 4 is a flow diagram of an example of a method of assigning identifiers to mental state values produced using the method of FIG. 2.

For some applications, however, it may be advantageous to simultaneously display the average mental state values as well as some or all of the individual mental state values for members of the group. In these examples, individual mental state values can also be output in step 174 to a user interface device (e.g., user interface 26 of mental state classifier 20) in addition to the average mental state values generated in steps 170-172.

Where mental state values for individual group members are also output in step 174, the individual mental state values can be assigned an identifier that enables identification of the group member to which those mental state values correspond. FIG. 4 is a flow diagram of method 250, which is a method of assigning identifiers to mental state values generated during method 100. Method 250 includes steps 252-254 of generating an identifier (step 252) and assigning the identifier to mental state values (step 254). Method 250 can be used to generate an identifier describing any individual for which mental state values are predicted using method 100 (e.g., any of the first, second, and third individuals), but will be described with respect to a generic individual for explanatory purposes.

In step 252, an identifier is generated based on at least one of the image data, audio data, and semantic text data extracted from the video data and corresponding to the individual. The identifier can be, for example, a name or other identifying information stored in metadata associated with the image data, audio data, and/or semantic text data. The identifier can also be, for example, a hair, color, eye color, or another visual property of the individual that can be detected within the image data.

In step 254, the identifier generated in step 252 is assigned to the mental state values associated with the individual. The identifier assigned to the mental state values can be stored to memory 24 and associated with the mental state values, such that a program executed by processor 22 of mental state classifier 20 (FIG. 1) can recall the identifier based on a mental state value to which the identifier is assigned. As such, programs accessing the mental state values generated by method 100 can perform analysis (e.g., statistical analysis) of the mental state values, select mental state values based on the results of the analysis, and recall identifiers associated with the selected mental state values. The identifier can be assigned to a mental state value in step 254 by, for example, by linking the identifier to the mental state value or by otherwise associating the identifier and the mental state values using a table, array, or matrix, among other options.

In addition to outputting mental state values and average mental state values, method 100 can include steps directed toward performing other analyses of group and individual mental state values. Step 176 is an optional step of method 100 in which additional analysis of group and individual mental state values is performed. Specifically, in optional step 176, outlier mental state values are identified. As used to herein, and as will be explained in more detail subsequently, an "outlier" mental state value refers to a mental state values (e.g., one of the first, second, third, fourth, fifth, or sixth mental state values) that differs from their respective average mental state value by more than a threshold value. Processor 22 of mental state classifier 20 (FIG. 1) can perform step 176 using one or more programs of outlier identification module 72.

For example, any of the first, second, and/or fifth mental state values that differ from the first average mental state value by more than a threshold value can be identified as an outlier. Similarly, any of the third, fourth, and/or sixth mental state values that differ from the second average mental state value by more than a threshold value can be identified as an outlier. The same threshold value can be used to evaluate outliers with respect to the first and second mental states or, in some examples, different threshold values can be used to evaluate outliers for each of the first and second mental states.

Any outliers identified in step 176 can be assigned an identifier and the identifier can be output to an individual interacting with the group. Identification of outliers advantageously enables an individual interacting with the group to understand which individuals are not represented by the average group mental state values without requiring representation or output of all mental state values for all individuals in the group. For groups having relatively few outliers as compared to group members, the identification of outliers enables an individual interacting with the group to be alerted to individuals that are not adequately represented by the average mental state values created in steps 170-172 without the requiring display of all mental state values and the associated disadvantageous cognitive burden discussed previously with respect to steps 170-174. Further, the automatic identification of outliers enables an individual interacting with the group to be alerted to individuals that significantly differ from the average mental state value without requiring that individual to use cognitive capacity to manually compare mental state values to the average mental state value. For example, the average mental state values for a group may indicate that the group on average is focused and attentive to presented material, but outlier information can indicate to a public speaker or presenter communicating information to the group that one or more individuals are not actually focused and attentive, allowing the public speaker or presenter to adjust their presentation strategy to attempt to engage those unengaged, outlier individuals.

Figure 5:
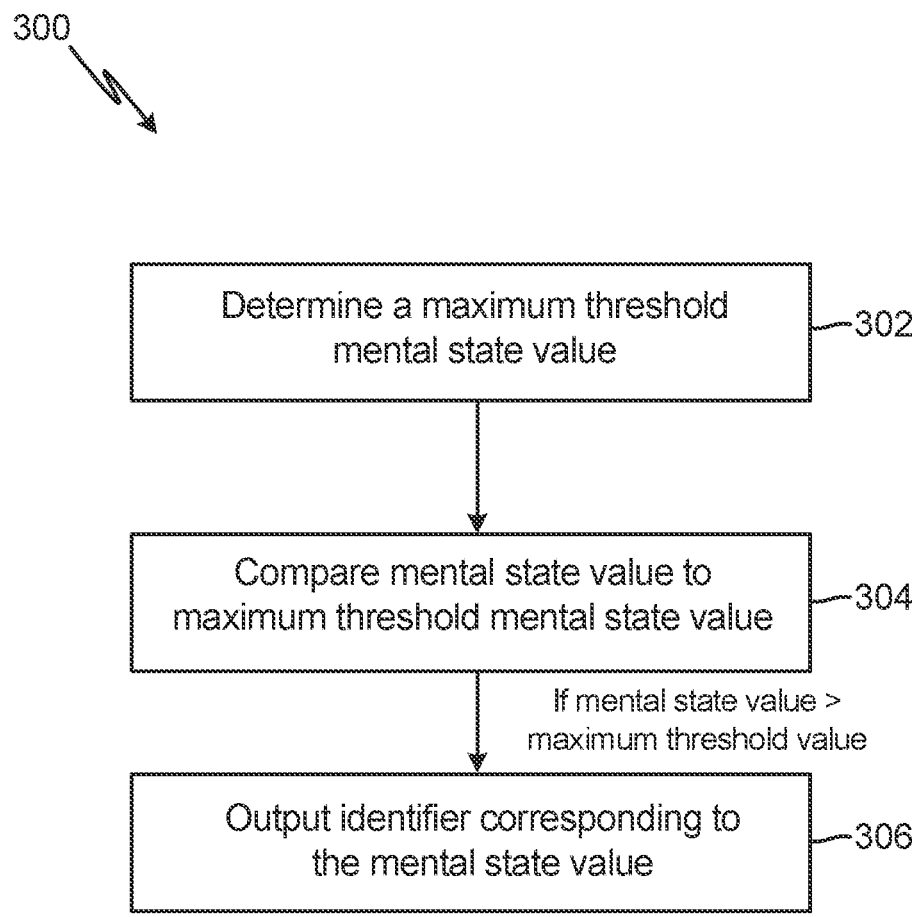
FIG. 5 is a flow diagram of an example of a method of identifying outliers suitable for use with the method of FIG. 2.

FIG. 5 is a flow diagram of method 300, which is a method of determining whether a mental state value is an outlier and can be used to perform step 176 of method 100. Method 300 includes steps 302-306 of determining a maximum threshold mental state value (step 302), comparing mental state values to the maximum threshold value (step 304), and outputting identifiers corresponding to mental state values greater than the maximum threshold value (step 306). Processor 22 of mental state classifier 20 (FIG. 1) can perform method 300 using one or more programs of outlier identification module 72. For explanatory purposes, method 300 will be described with respect to a generic mental state value and a generic average mental state value, but method 300 can be used with any individual and average mental state values generated using method 100 in order to determine whether the mental state value is an outlier.

In step 302, a maximum threshold mental state value is determined. The maximum threshold mental state value represents the maximum value of a mental state value for which the average mental state value is representative. Accordingly, values greater than the maximum threshold mental state value can be identified as outliers. The maximum threshold mental state can be determined by multiplying the average mental state value (i.e., an average mental state value determined in step 170 or 172 of method 100) by a reference value. For example, the reference value can be a value of 1.1, such that multiplying the average mental state value by the reference value produces a value that is 10% higher than the average mental state value. As such, an individual mental state value (e.g., a value generated in one of steps 142, 144, 146, 148, 164, or 168 of method 100) that exceeds the maximum threshold mental state value is more than 10% greater than the average mental state value, indicating that the individual mental state value is an outlier and should be treated separately from the average mental state value.

In other examples, the maximum threshold mental state value can be determined by multiplying an ideal mental state value by the reference value. The ideal mental state value can be determined by, for example, measuring mental state values of a plurality of individuals having desirable behavior, mental state, or other characteristics for a given application or operational need and creating an average mental state value based on the plurality of measured mental state values. The average mental state value can be stored to a memory, such as memory 24 of mental state classifier 20, for use as an ideal mental state value.

In step 304, the individual mental state value is compared to the maximum threshold value generated in step 302. If the individual mental state value is greater than the maximum threshold mental state value determined in step 302, method 300 progresses to step 306. If individual mental state value is less than the maximum mental state value, method 300 does not progress to step 306 and method 300 stops.

In step 306, an identifier corresponding to the individual mental state value is output. The identifier can be recalled from a memory, such as memory 24 of mental state classifier 20, and can be output to a user interface, such as user interface 26 of mental state classifier 20. The identifier describes the individual with which the mental state value is associated, as described previously with respect to method 250 (FIG. 4). The identifier can be generated and assigned the mental state value using method 250 (FIG. 4) or any other suitable method.

Figure 6:
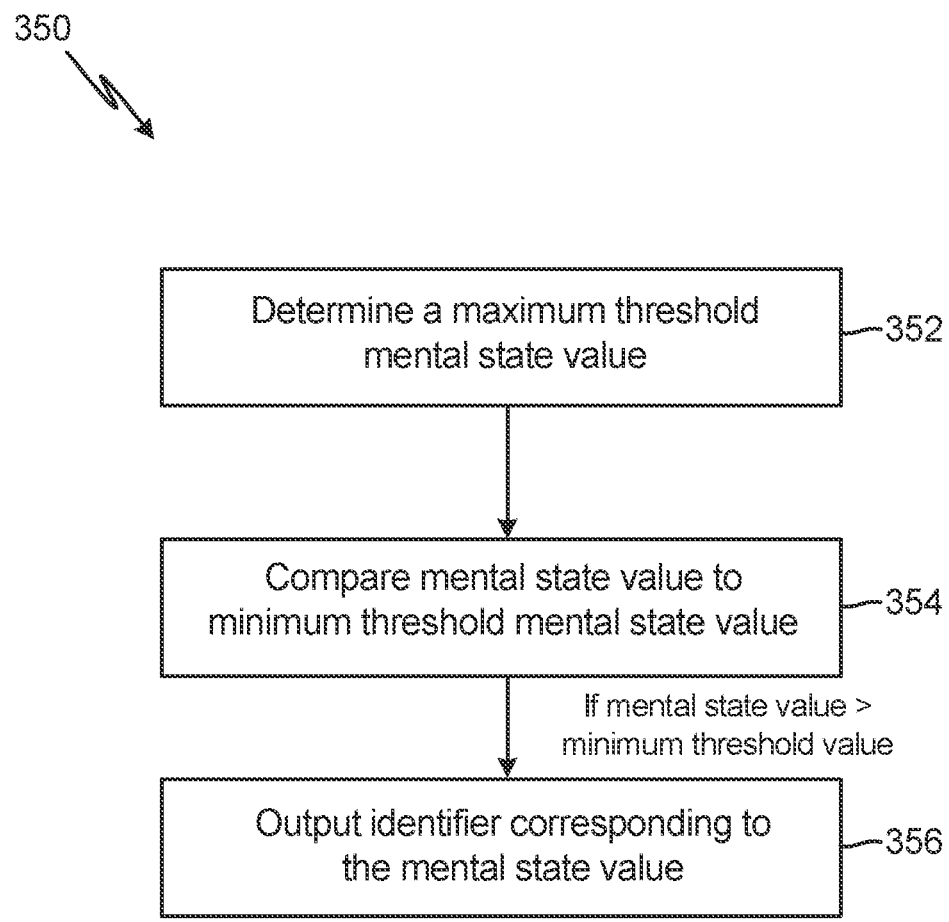
FIG. 6 is a flow diagram of another example of a method of identifying outliers suitable for use with the method of FIG. 2.

FIG. 6 is a flow diagram of method 350, which is another method determining whether a mental state value is an outlier. Like method 300, method 350 can also be used during step 176 of method 100. Processor 22 of mental state classifier 20 (FIG. 1) can perform method 350 using one or more programs of outlier identification module 72. Method 350 includes steps 352-356 of determining a minimum threshold mental state value (step 302), comparing mental state values to the minimum threshold value (step 304), and outputting identifiers corresponding to mental state values less than the minimum threshold value (step 306). For explanatory purposes, method 300 will be described with respect to a generic mental state value and a generic average mental state value, but method 300 can be used with any individual and average mental state values generated using method 100 in order to determine whether the mental state value is an outlier.

In step 352, the minimum threshold mental state value is determined. The minimum threshold mental state value represents the minimum value of a mental state value for which the average mental state value is representative. Accordingly, values less than the minimum threshold mental state value can be identified as outliers. The minimum threshold mental state value can be determined by multiplying the average mental state value (i.e., an average mental state value determined in step 170 or 172 of method 100) by a reference value. For example, the reference value can be a value of 0.9, such that multiplying the average mental state value by the reference value produces a value that is 10% lower than the average mental state value. As such, an individual mental state value (e.g., a value generated in one of steps 142, 144, 146, 148, 164, or 168 of method 100) that is lower than the threshold mental state value is more than 10% less than the average mental state value, indicating that the individual mental state value is an outlier and should be treated separately from the average mental state value.

In other examples, the minimum threshold mental state value can be determined by multiplying an ideal mental state value by the reference value. The ideal mental state value can be determined as outlined previously with respect to step 302 of method 300.

In step 354, the individual mental state value is compared to the minimum threshold value generated in step 352. If the individual mental state value is less than the minimum threshold mental state value determined in step 352, method 350 progresses to step 356. If individual mental state value is greater than the minimum mental state value, method 350 does not progress to step 356 and method 350 stops.

In step 306, an identifier corresponding to the individual mental state value is output. The identifier can be recalled from a memory, such as memory 24 of mental state classifier 20, and can be output to a user interface, such as user interface 26 of mental state classifier 20. As described previously with respect to step 306 of method 300 (FIG. 5) and with respect to method 250 (FIG. 4), the identifier describes the individual with which the mental state value is associated. The identifier can be generated and assigned the mental state value using method 250 (FIG. 4) or any other suitable method.

Figure 7:
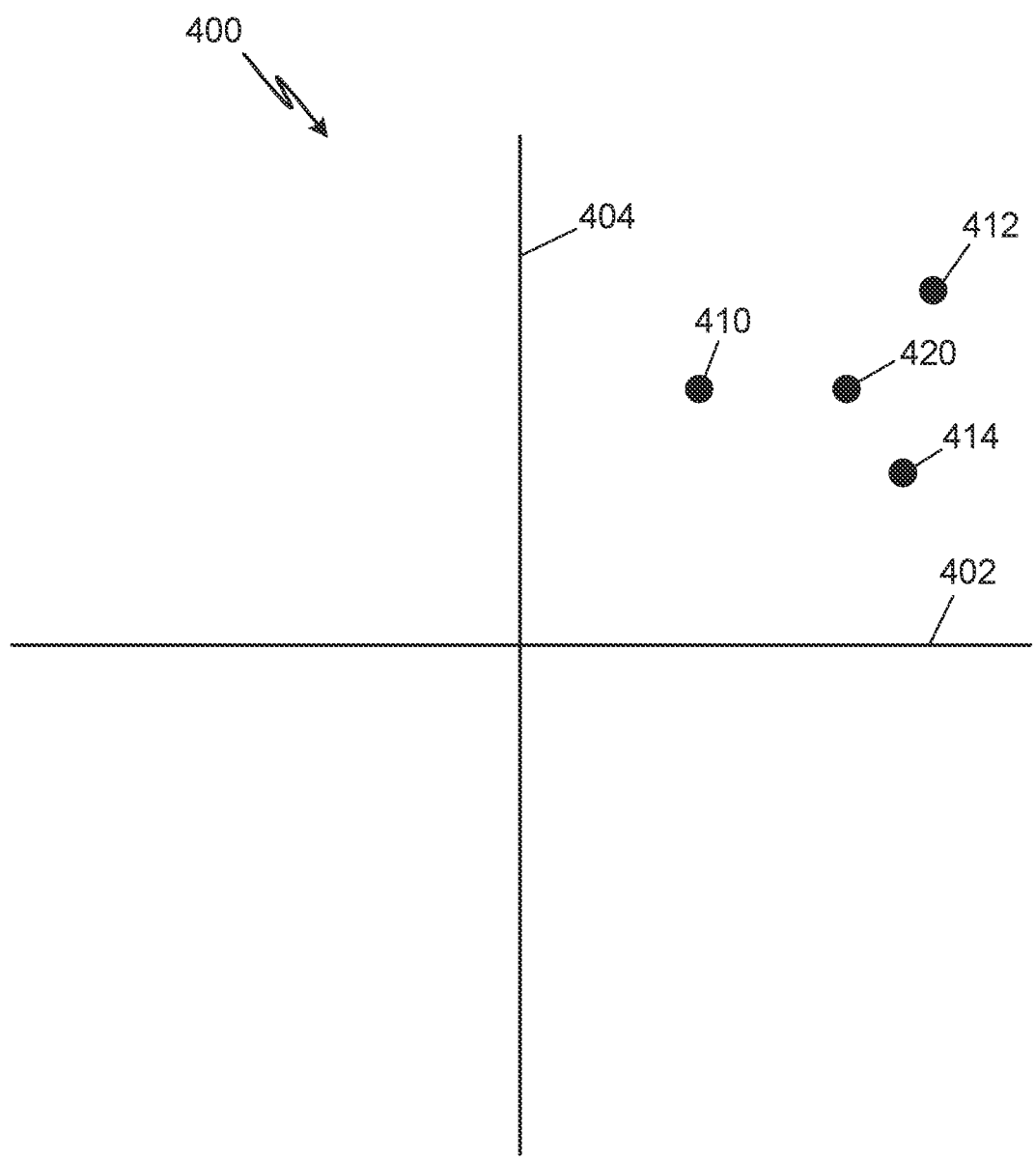
FIG. 7 is a schematic diagram of a multidimensional state model and mental state values produced using the method of FIG. 2.

Returning to method 100 (FIG. 2), steps 182-186 relate to the use of a multidimensional mental state model to analyze and visualize both individual and average mental state values. FIG. 7 is a schematic diagram of multidimensional mental state model 400, which includes first dimension 402, second dimension 404, first mental state point 410, second mental state point 412, third mental state point 414, and average mental state point 420. Multidimensional mental state model 400 is one example of a multidimensional mental state model suitable for use with steps 182-186 of method 100 and for explanatory purposes, steps 182-186 will be explained with reference to multidimensional mental state model 400. However, steps 182-186 can be adapted to be used with other multidimensional mental state models. Processor 22 of mental state classifier 20 (FIG. 1) can use one or more programs of group mental state prediction module 70 with a multidimensional mental state model, such as multidimensional mental state model 80 or 400, to perform each of steps 182-186.

As used herein, a "multidimensional mental state model" refers to a model of mental state that assigns different aspects of mental state to different dimensions of the model. Advantageously, multidimensional mental state models describe mental state more accurately than existing models of mental state. Because mental state models more accurately describe an individual's mental state, multidimensional mental state models significantly improve the resolution and accuracy of predictions of mental state as compared to existing models, including single-dimensional models of mental state. Referring to multidimensional mental state model 400, first dimension 402 can represent a first mental state, such as confusion, and second dimension 404 can represent a second mental state, such as calmness. Various regions of multidimensional mental state model 400 can represent different combinations of confusion and calmness, with each region representing a discrete overall mental state. For example, different quadrants can represent different overall states.

As a specific example, a quadrant with positive confusion and calmness values can represent an overall "confused and attentive" mental state; a quadrant with negative confusion and calmness values can represent an overall "comprehending and attentive" mental state; a quadrant with negative confusion and negative calmness can represent an overall "comprehending and inattentive" mental state; and a quadrant with positive confusion and negative calmness can represent an overall "confused and inattentive" mental state.

In other examples, the dimensions of multidimensional mental state model 400 can represent any other combination of mental states. For example, the dimensions of multidimensional mental state model 400 can be one or more of tiredness, sleepiness, serenity, satisfaction, calmness, relaxation, contentment, distress, frustration, anger, annoyance, tension, fear, alarm, misery, sadness, depression, gloom, boredom, astonishment, amusement, excitement, happiness, delight, gladness, pleasure, thankfulness, gratitude, confusion, smugness, deliberation, anticipation, cheer, sympathy, trust, humor, envy, melancholy, hostility, resentment, revulsion, and/or ennui. Additionally and/or alternatively, the dimensions of multidimensional mental state model 400 can represent specific aspects of mental state, such as the intensity of the individuals' mental state and/or the pleasantness of the individual's mental state. The dimensions of multidimensional mental state model 400 can also represent mental state by describing aspects of information communicated by the individual (i.e., in the image data, audio data, and/or semantic text data for an individual), such as the relative importance of the information the individual is conveying information, the positivity of the information the individual is conveying, and/or the subject of the conversation in which the individual is participating (e.g., whether the subject is administrative, technical, etc.), among other options.

Notably, as different types of data (i.e., image, audio, and semantic text) can be used to generate mental state values for the first and second mental states during method 100 (FIG. 2), different dimensions of the multidimensional mental state model can accordingly correspond to different types of data. The use of different combinations of the three types of information present in video data provides further advantages and improvements to both the efficiency and accuracy of the multidimensional mental state model. More specifically, excluding different combinations of image, audio, and text data allows non-predictive information to be disregarded for calculation of a dimensional value for a given dimension of the multidimensional mental state model, simultaneously improving the efficiency and accuracy with which mental state is determined. For example, text data may offer significantly more insight into the importance of a particular discussion than image or audio data. The multidimensional mental state model can be configured so that only the information classifier derived from the text data is used to calculate the dimension associated with discussion importance, improving accuracy by disregarding non-predictive data and, consequently, improving efficiency by only requiring one type of data to calculate the dimensional value for the discussion importance dimension.

These examples highlight the manner in which multidimensional mental state model 400 provides improved granularity and resolution of mental state as compared to existing models. As multidimensional mental state model 400 is able to more clearly distinguish between mental states having similar values along one dimension, multidimensional mental state model 400 is also able to represent a more complex set of mental states than existing mental state models using a single-dimension. Further, the inclusion of multiple dimensions significantly improves the resolution of multidimensional mental state model 400 by more clearly differentiating between different mental states than existing models. The improved resolution of multidimensional mental state model 400 allows for in significantly more accurate predictions of mental state than existing models.

In some examples, multidimensional mental state model 400 can be further divided into subregions can that correspond to more specific mental states. In some of these examples, the regions of multidimensional mental state model 400 that correspond to specific mental states can extend into multiple quadrants of multidimensional mental state model 400.

While multidimensional mental state model 400 is depicted in FIG. 4 as only including first dimension 402 and second dimension 404, additional dimensions can be added to multidimensional mental state model 400 as required for a given application and/or operational need. Adding additional dimensions to multidimensional mental state model 400 can allow nearby or similar mental states to be further distinguished, thereby improving the resolution of multidimensional mental state model 400. For example, additional dimensions describing information importance, information positivity, the subject of the information (i.e., whether the information is administrative, technical, etc.), and/or other mental states can further be used to resolve and distinguish between similar overall mental states. In examples where each dimension of the multidimensional mental state model represents a separate mental state (e.g., one or more of confusion, envy, calmness, sleepiness, etc.), the inclusion of additional dimensions can also allow for more accurate description of an individual's mental state.

In examples where each dimension of the multidimensional mental state model represents a separate mental state (e.g., one or more of confusion, envy, calmness, sleepiness, etc.), adding additional mental state can also allow for more accurate description of an individual's mental state. For example, a three-dimensional mental state model can describe three separate mental states that an individual may be experiencing simultaneously and that contribute to the individual's overall mental state. Similarly, a four-dimensional mental state model can describe four separate mental states and a five-dimensional mental state model can describe five separate mental states. Other examples of mental state models with more than five dimensions are contemplated herein.

In the example depicted in FIG. 7, multidimensional mental state model includes mental state points 410-414 and average mental state point 420. With reference to the mental state values generated in method 100 (FIG. 2), first mental state point 410 represents the first and third mental state values generated in steps 142 and 146, second mental state point 412 represents the second and fourth mental state values generated in steps 144 and 148, third mental state point 414 represents the fifth and sixth mental state values generated in steps 164 and 168, and average mental state point 420 represents the average mental state values generated in steps 170-172. To this extent, first mental state point 410 represents the overall mental state of the first individual, second mental state point 412 represents the overall mental state of the second individual, third mental state point 414 represents the overall mental state of the third individual, and average mental state point 420 represents the overall group mental state.

In some examples, step 176 can be performed by outputting the average mental states generated in steps 170, 172 and the mental state values generated in steps 142, 146 as a first point, the values generated in steps 144, 148 as a second point, and the values generated in steps 164, 168 as a third point on a graphical representation of multidimensional mental state model 400. For example, multidimensional mental state model 400 can be recalled from a memory, such as memory 24 of mental state classifier 20 (FIG. 1) and displayed as a diagram on a user interface, such as user interface 26 of mental state classifier 20. Control circuitry and/or a processor, such as processor 22 of mental state classifier 20 (FIG. 1), can cause the user interface to also display mental state points 410-414 to represent the mental states of the three individuals analyzed using method 100 as well as average mental state point 420. An individual interacting with the group can use mental state points 410-414 and average mental state point 420 to quickly understand the relative positions of each individual in the group as well as the relative position of the average group mental state along multidimensional mental state model 400.

In the depicted example, mental state points 410-414 and average mental state point are depicted as circular icons. In other examples, differently-shaped icons can be used distinguish mental state points 410-414 from average mental state point 420, and in further examples each of mental state points 410-414 and average mental state can have a unique icon. Additionally and/or alternatively, the icons for mental state points 410-414 can have a different color than average mental state point 420, or each of mental state points 410-414 and average mental state point 420 can be represented by a differently-colored icon.

Mental state points 410-414 can be labeled with identifier information generated using method 250 (FIG. 4) to enable an individual interacting with the group to more quickly ascertain the mental state of each individual in the group. Additionally and/or alternatively, mental state points 410-414 can be labeled to identify that the mental state point 410-414 includes an outlier, as identified in step 176 of method 100 (FIG. 2). Mental state points 410-414 can be labeled to indicate the dimension of multidimensional mental state model 400 in which the point includes an outlier value. Additionally and/or alternatively, mental state points 410-414 can be represented by differently-colored or differently-shaped icons to indicate that the point include an outlier value and/or to indicate which dimension of the point corresponds to an outlier value.

While the depiction of multidimensional mental state model 400 in FIG. 7 only includes three mental state points 410-414, in examples where method 100 (FIG. 2) is used to produce more three sets of mental state values (i.e., where method 100 is used to analyze more than three individuals forming a group), the user interface can also display additional points corresponding to other individuals analyzed using method 100.

Returning to method 100 (FIG. 2), a multidimensional mental state model is recalled in step 182. The multidimensional mental state model has dimensions corresponding to each of the average mental state values generated in steps 170-172. The multidimensional mental state model has at least two dimensions and can include more than two dimensions in examples of method 100 where more than two aspects of mental state are predicted and more than two average mental state values are generated. The multidimensional mental state model can be, for example, multidimensional mental state model 400. The multidimensional mental state model can be recalled from memory 24 of mental state classifier 20 (FIG. 1) or another suitable storage medium.

In step 184, an overall group mental state is generated. The overall group mental state is generated using the multidimensional mental state model and the average mental state values generated using method 100. As described previously with respect to FIG. 7, a multidimensional mental state model can be divided into regions of different first and second mental state values that correspond to different overall mental states. The average mental state values generated using method 100 can be compared against stored region data for the multidimensional mental state model to determine the overall group mental state. In some examples, the overall group mental state can be generated using a machine learning model trained to predict group mental state based on average mental state values, the multidimensional mental state model, and the average mental state values.

In step 186, the overall group mental state is output. The overall group mental state can be output via, for example, user interface 26 of mental state classifier 20 or another suitable user interface. The overall group mental state can be output as one or more displayed words, symbols, and/or icons. Additionally and/or alternatively, the overall group mental state can be output as audio describing the overall group mental state.

Steps 190-192 are optional and are used to augment video to represent individual and/or group mental states predicted using method 100. In examples where steps 190-192, the mental state predictions made using method 100 can be output as, for example, text, one or more images, one or more icons, or one or more symbols, among other options. Processor 22 of mental state classifier 20 (FIG. 1) can perform steps 190-192 and the augmented video can be output using, for example, user interface 26. Processor 22 can use one or more programs of video reconstruction module 76 to perform steps 190-192.

In step 190, the video data acquired in step 102 is augmented based on the overall group mental state generated in step 142, the average mental state values generated in steps 170 and/or 172, and/or the individual mental state values generated in steps 142, 144, 146, 148, 164, and/or 168. The video data is augmented according to the value of the average mental state values. For example, the video data can be augmented by displaying the one or more outputs of method 100 overlaid on the video data. Additionally and/or alternatively, the images and/or audio of the video data can be augmented to emphasize the mental state values generated for the group and/or for any individuals in the group. For example, the color of the background of the image data can be changed according to the overall group mental state. As a further example, additional image data can be added to portions of the image data corresponding to the first, second, and/or third individual to indicate the mental state values generated in steps 142, 144, 146, 148, 164, and/or 168 (e.g., by adding picture or symbol data that represents the individual's mental state). Similarly, one or more portions of the audio data can be enhanced according to the predicted mental state values. For example, a vocal effect or audio filter (e.g., delay, distortion, echo, pitch shift, pitch quantization, etc.) can be applied to the audio based on the overall and/or average mental state values generated in steps 182, 170, and/or 172. As a further example, a vocal effect or audio filter can be applied to audio corresponding to particular individuals in the video data according to their predicted mental state values.

In step 192, the augmented video is output. The augmented video can be output to a user interface, such as a display or audio device of user interface 26. The output video can be displayed to group members, other users, and/or individuals interacting with the group in addition to or place of the original video data acquired in step 202. Where the group is, for example, a lecture or presentation audience, the enhanced video can be output through an audiovisual device to the lecturer or presenter. Where the group is, for example, taking part in a video conference through the videoconferencing software, the augmented video can be output through the videoconferencing software to visually and/or aurally communicate each individual's mental state to other members of the videoconference as well as to visually and/or aurally communicate the overall group mental state. Individuals interacting with the group and/or group members can use the augmented video output to adjust their interaction with the group as a whole and/or with particular group members.

Method 100 can be iterated in time-based intervals over the course of an interaction captured by video. In some examples, method 100 can iterated in very short time intervals such that method 100 can be performed in real-time or substantially in real-time. In these examples, the predicted mental states created using method 100 can be presented in real-time or substantially real-time, improving understanding for individuals with and without perception impairments and enabling individuals to act on a predicted individual or group mental state in real-time or in substantially real-time.

In some examples, data from method 100 can be tracked over time to determine trends in average group mental state or overall group mental state predictions. The trends identified by tracking data from method 100 can be used to improve group performance, identify problems in group dynamics, or determine new strategies for interacting with a group. For example, a group leader can use time-resolved data from method 100 to understand how dynamics of the group have changed over the course of one or more meetings of the group. As a further example, a presenter interacting with the group can use time-resolved data from method 100 to evaluate the effectiveness of their presentation techniques over one or more presentations and/or to evaluate the effectiveness of adjustments to their presentation techniques over the course of several presentations.

Advantageously, method 100 allows prediction of mental state based solely on video data of an individual rather than on biometric measurements or other more invasive measurement techniques. Further, as method 100 can be configured to use a multidimensional mental state model, the advantages of which are outlined in detail previously and particularly with respect to FIG. 7, method 100 provides numerous advantages over existing models of mental state. Particularly, the multidimensional mental state models that can be used by method 100 are scalable and can include any number of dimensions based on operational need. The dimensions can advantageously include any combination of mental states, mental state components, factors that contribute to mental state, and aspects of communicated information based on application or operational need.

Method 100 provides further benefits to accessibility for individuals having perception impairments, such as impairments to speech or vision. Perception-impaired people can experience difficulty in reading facial expressions or understanding emotions expressed in speech. Method 100 enables the display of machine-generated mental state predictions that can be displayed or otherwise communicated to a hearing-, vision-, and/or perception-impaired individual to improve understanding of, for example, how a group (e.g., a crowd or audience) is reacting to presented content, the overall group temperament, and which individuals in a group are outliers among the group.

Figure 8:
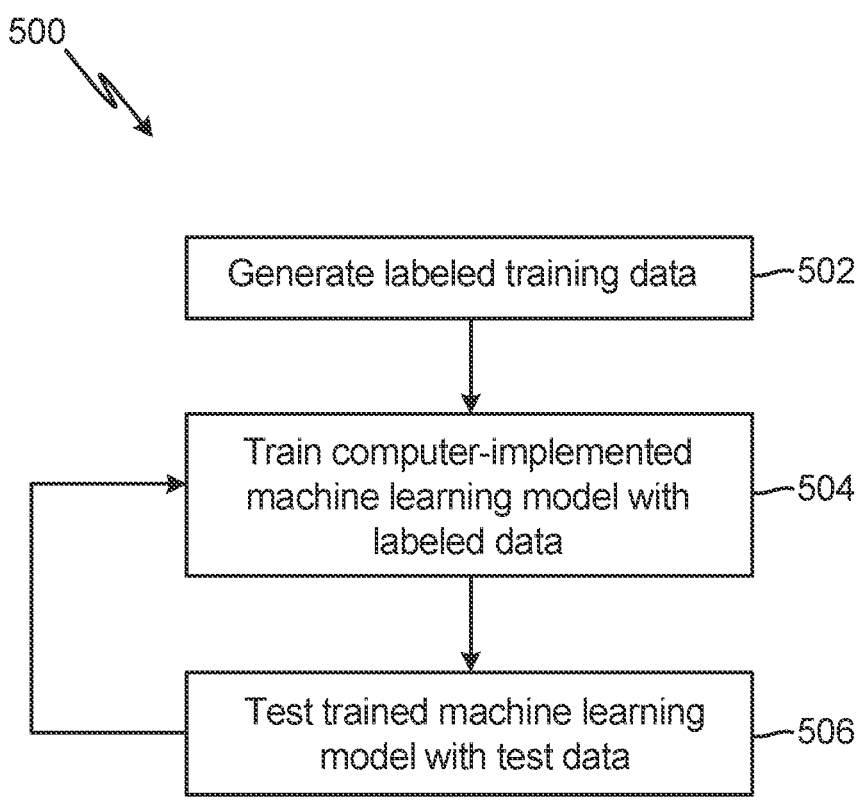
FIG. 8 is a flow diagram of an example of a method of training a computer-implemented machine learning model suitable for use with other methods of this disclosure.

FIG. 8 is a flow diagram of method 500, which is a method of training a computer-implemented machine learning model. Method 500 includes steps 502-506 of generating labeled training data (step 502), training the computer-implemented machine learning model with the labeled data (step 504), and testing the trained computer-implemented machine learning model with test data (step 506). Method 500 can be used to train any machine learning model described herein (e.g., for a machine learning model for generating any individual mental state value, for identifying features for a feature set, etc.), but will be discussed with respect to a generic machine learning model for explanatory purposes.

In step 502, labeled data is generated. The labeled data can be, for example, audio data, image data, semantic text data, or labeled outputs of another trained machine learning model. The labeled data can be labeled according to the types of mental state values predicted using method 100. For example, one machine learning model can be trained with data labeled according to the first mental state and a second machine learning model can be trained with data labeled according to the second mental state, such that the first machine learning model can later be used to predict the first, second, and fifth mental state values in steps 142, 144, and 164, and the second machine learning model can be used to predict the third, fourth, and sixth mental state values in steps 146, 148, and 168.

In step 504, the labeled data is used to train the computer-implemented machine learning model. As used herein, "training" a computer-implemented machine learning model refers to any process by which parameters, hyper parameters, weights, and/or any other value related model accuracy are adjusted to improve the fit of the computer-implemented machine learning model to the training data.

In step 506, the trained computer-implemented machine learning model is tested with test data. The test data used in step 506 is unlabeled data that is used to qualify and/or quantify performance of the trained computer-implemented machine learning model. More specifically, a human or machine operator can evaluate the performance of the machine learning model by evaluating the fit of the model to the test data. Step 506 can be used to determine, for example, whether the machine learning model was overfit to the labeled data during model training in step 504.

As depicted in FIG. 5, steps 504 and 506 can be performed iteratively to improve the performance of the machine learning model. More specifically, if the fit of the model to the unlabeled data determined in step 506 is undesirable, step 504 can be repeated to further adjust the parameters, hyper parameters, weights, etc. of the model to improve the fit of the model to the test data. Step 506 can then be repeated with a new set of unlabeled test data to determine how the adjusted model fits the new set of unlabeled test data. If the fit continues to be undesirable, further iterations of steps 504 and 506 can be performed until the fit of the model becomes desirable.

The methods and systems disclosed herein advantageously allow for the training and use of a series of machine learning models that can predict the mental state of individuals and groups captured in video data. Advantageously, the use of computer-implemented machine learning models enables method 100 to be performed in real-time or substantially in real-time. As described previously, method 100 can be iterated in time-based intervals over the course of an interaction captured by video. Where method 100 is performed in real-time or substantially in real-time, the predicted mental states created using method 100 can be presented in real-time or substantially real-time, improving understanding for individuals with and without perception impairments and enabling individuals to act on an individual's predicted mental state in real-time or in substantially real-time.

Further, the methods and systems disclosed herein allow for the generation of a simplified values (i.e., average group mental state values and/or overall group mental state predictions) that represent the overall mental state of all individuals in a group. Advantageously, this enables both outside individuals interacting with the group as well as group members to quickly ascertain a general predicted group mental state without requiring inspection of all predicted mental states for all individuals in the group. Where the group is large, the systems and methods disclosed herein significantly simplify the process by which an individual can understand overall group state of mind or temperament.

Notably, as described previously, the use of a multidimensional mental state model, such as multidimensional mental state model 400, provides significant advantages over existing methods of determining mental state, including existing methods that utilize multiple machine learning models and/or multiple types of data capturing the individual (e.g., image data, audio data, and/or text data). Specifically, a multidimensional mental state model according to the present disclosure improves the accuracy of mental state predictions and the efficiency with which mental state predictions can be computed. Further, a multidimensional mental state model provides significant flexibility over other existing mental state models and provides improved granularity and resolution, thereby further improving the accuracy of mental state predictions made using the multidimensional mental state model.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the present disclosure.

The invention claimed is:

1. A method of predicting a group mental state, the method comprising:
   acquiring video data of a first individual and a second individual;
   extracting first image data of the first individual from the video data;
   extracting first audio data of the first individual from the video data;
   extracting second image data of the second individual from the video data;
   extracting second audio data of the second individual from the video data;
   extracting first semantic text data from the first audio data;
   extracting second semantic text data from the second audio data;
   identifying, by a first computer-implemented machine learning model, a first set of features from at least one of the first image data, the first audio data, and the first semantic text data;
   identifying, by the first computer-implemented machine learning model, a second set of features from at least one of the second image data, the second audio data, and the second semantic text data;
   predicting, by a second computer-implemented machine learning model, a first mental state value based on the first set of features, wherein the first mental state value describes a first mental state;
   predicting, by the second computer implemented machine learning model, a second mental state value based on the second set of features, wherein the second mental state value describes the first mental state;
   predicting, by a third computer implemented machine learning model, a third mental state value based on the first set of features, wherein the third mental state value describes a second mental state;
   predicting, by the third computer implemented machine learning model, a fourth mental state value based on the second set of features, wherein the fourth mental state value describes the second mental state;
   generating a first average mental state value by averaging the first mental state value and the second mental state value; and
   generating a second average mental state value by averaging the third mental state value and the fourth mental state value.

2. The method of claim 1, further comprising outputting the first and second average mental state values.

3. The method of claim 1, further comprising displaying, by a user interface device, a graphical representation of a point having a first point value along a first axis and a second point value along a second axis, wherein the first point value is based on the first average mental state value and the second point value is based on the second average mental state value.

4. The method of claim 1, further comprising:
   recalling, from a memory, a multidimensional mental state model, wherein a first dimension of the multidimensional mental state model describes the first mental state and a second dimension of the multidimensional mental state model describes the second mental state; and
   generating an overall group mental state for a group comprising the first individual and the second individual based on the multidimensional mental state model, the first average mental state value, and the second average mental state value.

5. The method of claim 1, further comprising:
   augmenting a portion of the video data based on the first average mental state value and the second average mental state value; and
   outputting the augmented video data.

6. The method of claim 1, wherein the acquired video data is of the first individual, the second individual, and a third individual, and further comprising:
   extracting third image data of the third individual from the video data;
   extracting third audio data of the third individual from the video data;
   extracting third semantic text data from the third audio data;

identifying, by the first computer-implemented machine learning model, a third set of features from at least one of the third image data, the third audio data, and the third semantic text data;

predicting, by the second computer-implemented machine learning model, a fifth mental state value based on the third set of features, wherein the fifth mental state value describes the first mental state; and predicting, by the third computer implemented machine learning model, a sixth mental state value based on the third set of features, wherein the sixth mental state value describes the second mental state;

wherein:
the first average mental state value is generated by averaging the first mental state value, the second mental state value, and the fifth mental state value; and the second average mental state value is generated by averaging the third mental state value, the fourth mental state value, and the sixth mental state value.

7. The method of claim 6, and further comprising:
associating a first identifier with the first mental state value and the third mental state value;
associating a second identifier with the second mental state value and the fourth mental state value; and
associating a third identifier with the fifth mental state value and the sixth mental state value.

8. The method of claim 7, wherein:
the first identifier includes one or more features of the first set of features;
the second identifier includes one or more features of the second set of features; and
and the third identifier includes one or more features of the third set of features.

9. The method of claim 7, and further comprising:
determining a first maximum threshold value based on a first target deviation and the first average mental state value;
determining a second maximum threshold value based on a second target deviation and the second average mental state value;
comparing the first mental state value, second mental state value, and fifth mental state value to the first maximum threshold value; and
comparing the third mental state value, fourth mental state value, and sixth mental state value to the second maximum threshold value.

10. The method of claim 9, and further comprising:
outputting the first identifier if the first mental state value is greater than the first maximum threshold value, the third mental state value is greater than the second maximum threshold value, or both the first mental state is greater than the first maximum threshold value and the third mental state is greater than the second maximum threshold value;
outputting the second identifier if the second mental state value is greater than the first maximum threshold value, the fourth mental state value is greater than the second maximum threshold value, or both the second mental state is greater than the first maximum threshold value and the fourth mental state is greater than the second maximum threshold value; and
outputting the third identifier if the fifth mental state value is greater than the first maximum threshold value, the sixth mental state value is greater than the second maximum threshold value, or both the fifth mental state is greater than the first maximum threshold value and the sixth mental state is greater than the second maximum threshold value.

11. The method of claim 7, and further comprising:
determining a first minimum threshold value based on a first target deviation and the first average mental state value;
determining a second minimum threshold value based on a second target deviation and the second average mental state value;
comparing the first mental state value, second mental state value, and fifth mental state value to the first minimum threshold value; and
comparing the third mental state value, fourth mental state value, and sixth mental state value to the second minimum threshold value.

12. The method of claim 11, and further comprising:
outputting the first identifier if the first mental state value is less than the first maximum threshold value, the third mental state value is less than the second maximum threshold value, or both the first mental state is less than the first maximum threshold value and the third mental state is less than the second maximum threshold value;
outputting the second identifier if the second mental state value is less than the first maximum threshold value, the fourth mental state value is less than the second maximum threshold value, or both the second mental state is less than the first maximum threshold value and the fourth mental state is less than the second maximum threshold value; and
outputting the third identifier if the fifth mental state value is less than the first maximum threshold value, the sixth mental state value is less than the second maximum threshold value, or both the fifth mental state is less than the first maximum threshold value and the sixth mental state is less than the second maximum threshold value.

13. The method of claim 1, further comprising:
identifying the first individual based on at least one of the first image data, the first audio data, and the first semantic text data; and
identifying the second individual based on at least one of the second image data, the second audio data, and the second semantic text data.

14. The method of claim 1, wherein the first mental state and the second mental state are selected from a group consisting of tiredness, sleepiness, serenity, satisfaction, calmness, relaxation, contentment, distress, frustration, anger, annoyance, tension, fear, alarm, misery, sadness, depression, gloom, boredom, astonishment, amusement, excitement, happiness, delight, gladness, pleasure, thankfulness, gratitude, confusion, smugness, deliberation, anticipation, cheer, sympathy, trust, humor, envy, melancholy, hostility, resentment, revulsion, and ennui.

15. The method of claim 1, wherein the first set of features comprises one or more of:
a hand gesture;
head tilt;
an eyebrow position;
a mouth position;
a mouth shape;
a presence of eye contact;
an amount of eye blinking;
a speed of eye blinking; and
forehead wrinkling.

16. The method of claim 1, where in the first set of features comprises one or more of vocal tone, vocal pitch, intonation, inflection, and sentences stress.

17. The method of claim 1, wherein the first set of features comprises one or more of words, phrases, and sentences.

18. The method of claim 1, wherein:
the first mental state value describes a first intensity of the first mental state;
the second mental state value describes a second intensity of the first mental state;
the third mental state value describes a first intensity of the second mental state;
the fourth mental state value describes a second intensity of the second mental state;
the fifth mental state value describes a third intensity of the first mental state; and
the sixth mental state value describes a third intensity of the second mental state.

19. A system for predicting a group mental state, the system comprising:
processor;
a user interface configured to enable an operator to interact with the processor; and
a memory encoded with instructions that, when executed, cause the processor to:
acquire video data of a first individual and a second individual;
extract first image data of the first individual from the video data;
extract first audio data of the first individual from the video data;
extract second image data of the second individual from the video data;
extract second audio data of the second individual from the video data;
extract first semantic text data from the first audio data;
extract second semantic text data from the second audio data;
identify, by a first computer-implemented machine learning model, a first set of features from at least one of the first image data, the first audio data, and the first semantic text data;
identify, by the first computer-implemented machine learning model, a second set of features from at least one of the second image data, the second audio data, and the second semantic text data;
predict, by a second computer-implemented machine learning model, a first mental state value based on the first set of features, wherein the first mental state value describes a first mental state;
predict, by the second computer implemented machine learning model, a second mental state value based on the second set of features, wherein the second mental state value describes the first mental state;
predict, by a third computer implemented machine learning model, a third mental state value based on the first set of features, wherein the third mental state value describes a second mental state;
predict, by the third computer implemented machine learning model, a fourth mental state value based on the second set of features, wherein the fourth mental state value describes the second mental state;
generate a first average mental state value by averaging the first mental state value and the second mental state value; and
generate a second average mental state value by averaging the third mental state value and the fourth mental state value.

20. A method of predicting a group mental state, the method comprising:
acquiring video data of a first individual, a second individual, and a third individual;
extracting first image data of the first individual from the video data;
extracting first audio data of the first individual from the video data;
extracting second image data of the second individual from the video data;
extracting second audio data of the second individual from the video data;
extracting third image data of the third individual from the video data;
extracting third audio data of the third individual from the video data;
extracting first semantic text data from the first audio data;
extracting second semantic text data from the second audio data;
extracting third semantic text data from the third audio data;
identifying, by a first computer-implemented machine learning model, a first set of features from at least one of the first image data, the first audio data, and the first semantic text data;
identifying, by the first computer-implemented machine learning model, a second set of features from at least one of the second image data, the second audio data, and the second semantic text data;
identifying, by the first computer-implemented machine learning model, a third set of features from at least one of the third image data, the third audio data, and the third semantic text data;
predicting, by a second computer-implemented machine learning model, a first mental state value based on the first set of features, wherein the first mental state value describes a first mental state;
predicting, by the second computer implemented machine learning model, a second mental state value based on the second set of features, wherein the second mental state value describes the first mental state;
predicting, by a third computer implemented machine learning model, a third mental state value based on the first set of features, wherein the third mental state value describes a second mental state;
predicting, by the third computer implemented machine learning model, a fourth mental state value based on the second set of features, wherein the fourth mental state value describes the second mental state;
predicting, by the second computer-implemented machine learning model, a fifth mental state value based on the third set of features, wherein the fifth mental state value describes the first mental state;
predicting, by the third computer implemented machine learning model, a sixth mental state value based on the third set of features, wherein the sixth mental state value describes the second mental state;
generating a first average mental state value by averaging the first mental state value, the second mental state value, and the fifth mental state value;
generating a second average mental state value by averaging the third mental state value, the fourth mental state value and the sixth mental state value;

recalling, from a memory, a multidimensional mental state model, wherein a first dimension of the multidimensional mental state model describes the first mental state and a second dimension of the multidimensional mental state model describes the second mental state; and generating an overall group mental state for a group comprising the first individual, the second individual, and the third individual based on the multidimensional mental state model, the first average mental state value, and the second average mental state value.

* * * * *